United States Patent
Abe

(10) Patent No.: US 8,320,997 B2
(45) Date of Patent: Nov. 27, 2012

(54) VEIN AUTHENTICATION APPARATUS AND TEMPLATE REGISTRATION METHOD

(75) Inventor: Hiroshi Abe, Tokyo (JP)

(73) Assignee: Sony Corporation, Tokyo (JP)

(*) Notice: Subject to any disclaimer, the term of this patent is extended or adjusted under 35 U.S.C. 154(b) by 390 days.

(21) Appl. No.: 12/693,145

(22) Filed: Jan. 25, 2010

(65) Prior Publication Data

US 2010/0198078 A1    Aug. 5, 2010

(30) Foreign Application Priority Data

Feb. 4, 2009  (JP) ................. P2009-024239

(51) Int. Cl.
*A61B 5/00* (2006.01)
(52) U.S. Cl. ......... 600/473; 600/475; 382/115; 382/128
(58) Field of Classification Search .......... 600/473, 600/475; 382/115, 128
See application file for complete search history.

(56) References Cited

FOREIGN PATENT DOCUMENTS

| JP | 2001-067481 | 3/2001 |
|----|-------------|--------|
| JP | 2004-234355 | 8/2004 |
| JP | 2007-213427 | 8/2007 |
| JP | 2007-226549 | 9/2007 |
| JP | 2007-287080 | 11/2007 |

*Primary Examiner* — Ruth S Smith
(74) *Attorney, Agent, or Firm* — Finnegan, Henderson, Farabow, Garrett & Dunner, L.L.P.

(57) ABSTRACT

A vein authentication apparatus according to the present invention is provided with a vein pattern extraction unit for extracting a vein pattern from each of the plurality of vein image data, a rotational amount calculation unit for calculating a rotational direction and an amount of rotation of the finger, a registration information selection unit for calculating a shift width of the imaging range, and for determining whether the shift width of the imaging range is equal to or more than a predetermined threshold value, and for selecting a vein pattern to be registered as a template from among the plurality of vein patterns, and for setting the selected vein pattern as registration information, and a registration information compression unit for compressing, in accordance with the shift width of the imaging range, each of the plurality of selected registration information.

9 Claims, 16 Drawing Sheets

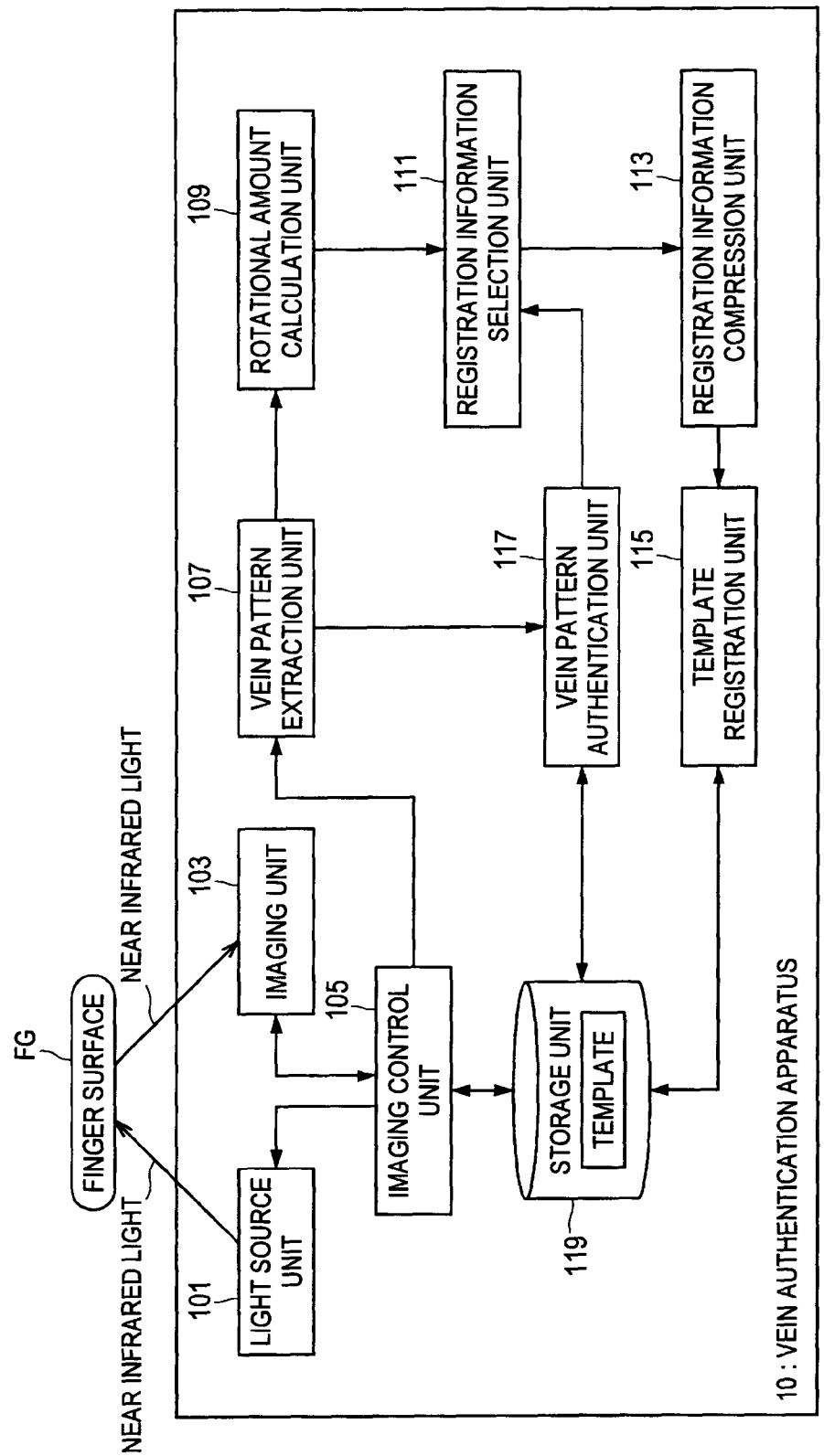

VEIN AUTHENTICATION APPARATUS AND TEMPLATE REGISTRATION METHOD

BACKGROUND OF THE INVENTION

1. Field of the Invention

The present invention relates to a vein registration apparatus and a template registration method.

2. Description of the Related Art

With the progress in information communication technology, various services such as electronic money and commuter pass are now available on a portable terminal such as a PDA (Personal Digital Assistant) and on a portable device such as a portable telephone. Various authentication methods can be used in order to ensure security in the use of these services.

Examples of these authentication methods include a vein authentication technique for authenticating an individual using a vein pattern obtained by imaging a portion of a living body. This vein authentication is expected as a next-generation biometric individual authentication because of its high accuracy in determination and its high resistance to counterfeit and spoofing.

In the biometric individual authentication, however, the same information is not necessarily input every time an authentication is performed, because a state of a living body and an environment at the time of the authentication may vary. Therefore, inputs within a certain distributional range should be assumed based on statistics, which makes it difficult to stably perform the authentication processing with standardized template information.

In view of the above circumstances, in the finger vein authentication, for example, Japanese Patent Laid-Open No. 2007-213427 discloses a method for stably performing an authentication by storing as templates multiple patterns, which are obtained by slightly rotating a finger is on its axis, i.e., in the longitudinal direction of the finger.

SUMMARY OF THE INVENTION

However, the above method described in Japanese Patent Laid-Open No. 2007-213427 has an issue in that, although a user does not have to bear a burden during the authentication, the user interface has to force the user to do awkward movements or unilaterally forces the user to do movements during the registration process.

In light of the foregoing, it is desirable to provide a vein authentication apparatus and a template registration method which make it possible to obtain template data in which different rotational shifts occur and by which a stable authentication processing can be realized, without forcing a user to do any awkward movement.

To solve the issues mentioned above, according to an embodiment of the present invention, there is provided a vein authentication apparatus including a light source unit for emitting a near infrared light having a predetermined wavelength to a surface of a finger rotating on its axis in a longitudinal direction, an imaging unit for imaging the finger surface, to which the near infrared light is emitted, at a predetermined time interval, for generating a plurality of vein image data whose imaging ranges are different from each other, a vein pattern extraction unit for extracting a vein pattern from each of the plurality of vein image data, a rotational amount calculation unit for calculating a rotational direction and an amount of rotation of the finger associated with the rotational movement for each of the extracted vein patterns by using an imaging range of one of the vein patterns as a reference, a registration information selection unit for calculating a shift width of the imaging range on the basis of the rotational direction and the amount of rotation, for determining whether the shift width of the imaging range is equal to or more than a predetermined threshold value and for selecting a vein pattern to be registered as a template from among the plurality of vein patterns when the shift width of the imaging range is less than the predetermined threshold value, and for setting the selected vein pattern as registration information, and a registration information compression unit for compressing, in accordance with the shift width of the imaging range, each of the plurality of pieces of registration information selected when the shift width of the imaging range is equal to or more than the predetermined threshold value.

With such configuration, a light source unit emits a near infrared light having a predetermined wavelength to a surface of a finger rotating on its axis in a longitudinal direction. An imaging unit images the finger surface, to which the near infrared light is emitted, at a predetermined time interval, and generates a plurality of vein image data whose imaging ranges are different from each other. A vein pattern extraction unit extracts a vein pattern from each of the plurality of vein image data. A rotational amount calculation unit calculates a rotational direction and an amount of rotation of the finger associated with the rotational movement for each of the extracted vein patterns by using an imaging range of one of the vein patterns as a reference. A registration information selection unit calculates a shift width of the imaging range on the basis of the rotational direction and the amount of rotation, and determines whether the shift width of the imaging range is equal to or more than a predetermined threshold value, and selects a vein pattern to be registered as a template from among the plurality of vein patterns when the shift width of the imaging range is less than the predetermined threshold value, and sets the selected vein pattern as registration information. A registration information compression unit compresses, in accordance with the shift width of the imaging range, each of the plurality of pieces of registration information selected when the shift width of the imaging range is equal to or more than the predetermined threshold value.

The registration information selection unit preferably sorts the plurality of pieces of registration information selected when the shift width of the imaging range is equal to or more than the predetermined threshold value, in ascending order from the registration information in which the amount of rotation has the smallest absolute value.

The registration information compression unit preferably causes an amount of data allocated for registering the registration information in which the amount of rotation has the smallest absolute value among the plurality of pieces of registration information, to be larger than an amount of data allocated for registering the other of the plurality of pieces of registration information.

The registration information compression unit preferably causes a compression rate of the registration information in which the amount of rotation has the smallest absolute value among the plurality of pieces of registration information, to be lower than a compression rate of the other of the plurality of pieces of registration information.

The registration information selection unit may hold the vein patterns located at both ends of the imaging range, and may select a vein pattern located in a position from which distances to adjacent registration candidates are close to be equal from among the vein patterns existing between the vein patterns located at the both ends.

The rotational amount calculation unit preferably calculates a correlation coefficient between the one of the vein patterns serving as the reference and the other of the vein patterns, and calculates the rotational direction and the amount of rotation on the basis of a shift direction and an amount of shift at a peak position of the correlation coefficient.

The threshold value of the shift width in the imaging range may be 10% of pixels representing an imaging range of the one of the vein patterns serving as the reference.

The vein authentication apparatus may further include a vein pattern authentication unit for authenticating the extracted vein pattern on the basis of the registration information registered as the template. The registration information selection unit may update the content of the already registered registration information by using the registration information and the authenticated vein pattern.

Further, to solve the issues mentioned above, according to another embodiment of the present invention, there is provided a template registration method including the steps of emitting a near infrared light having a predetermined wavelength to a surface of a finger rotating on its axis in a longitudinal direction, imaging the finger surface, to which the near infrared light is emitted, at a predetermined time interval and generating a plurality of vein image data whose imaging ranges are different from each other, extracting a vein pattern from each of the plurality of vein image data, calculating a rotational direction and an amount of rotation of the finger associated with the rotational movement for each of the extracted vein patterns by using an imaging range of one of the vein patterns as a reference, calculating a shift width of the imaging range on the basis of the rotational direction and the amount of rotation, determining whether the shift width of the imaging range is equal to or more than a predetermined threshold values, selecting the vein pattern to be registered as a template from among the plurality of vein patterns when the shift width of the imaging range is less than the predetermined threshold value, and setting the selected vein pattern as registration information, and compressing, in accordance with the shift width of the imaging range, each of the plurality of pieces of registration information selected when the shift width of the imaging range is equal to or more than the predetermined threshold value.

As described above, according to the present embodiment, it is possible to obtain template data in which different rotational shifts occur and by which a stable authentication processing can be realized, without forcing a user to do any awkward movement.

BRIEF DESCRIPTION OF THE DRAWINGS

FIG. 4 is a block diagram for illustrating a configuration of a vein authentication apparatus according to the embodiment;

DETAILED DESCRIPTION OF THE EMBODIMENTS

Figure 1A:
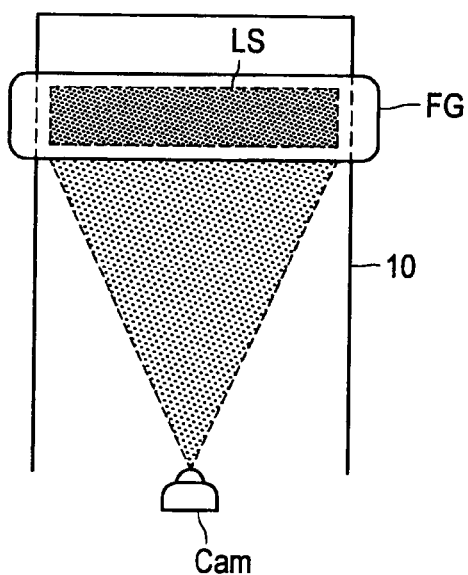
FIG. 1A is an explanatory diagram for illustrating an overview of a template registration method according to the first embodiment of the present invention.

Hereinafter, preferred embodiments of the present invention will be described in detail with reference to the appended drawings. Note that, in this specification and the appended drawings, structural elements that have substantially the same function and structure are denoted with the same reference numerals, and repeated explanation of these structural elements is omitted.

The explanation will be made in the following order.
(1) Purpose
(2) First Embodiment
  (2-1) Overview of template registration method
  (2-2) Configuration of vein authentication apparatus
  (2-3) Details of template registration method
  (2-4) Update of registered information during authentication processing
(3) Hardware configuration of vein authentication apparatus according to each embodiment of the present invention
(4) Summary
<Purpose>

Figure 18:
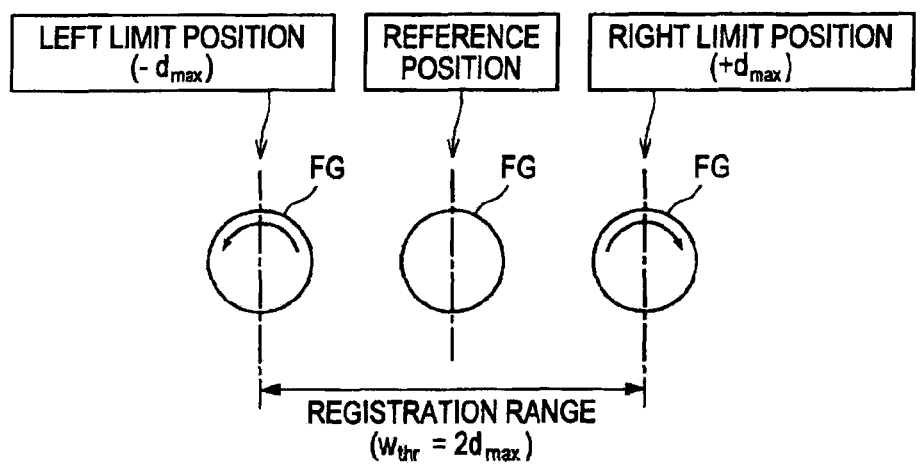
FIG. 18 is an explanatory diagram for illustrating a template registration method in related art.

Before explaining the vein authentication apparatus and the template registration method according to each embodiment of the present invention, issues and the like in a template registration method in related art will be first explained with reference to FIG. 18, and the purpose of the present invention will be described. FIG. 18 is an explanatory diagram for illustrating a templates registration method in related art.

In this exemplary template registration method in related art, for example, totally three images, i.e., left, right and center, are obtained, and different rotational shifts are obtained as template data.

In this method, a template serving as a reference is first determined as shown in FIG. 18. In other words, a finger in a stationary state is captured as a reference position, and a reference template is generated from the image in that state. Herein, the finger in the stationary state means that the finger is "stationary" in terms of imaged frames, which does not place a burden on a user. Next, as shown in FIG. 18, in a state where a finger is rotated to the right or left from the reference position, template data are registered as reference images at the position in which the predetermined rotation is achieved (i.e., the right and left rotation limit positions $\pm d_{max}$). In this method in related art, a registration range of a rotational shift $w_{thr}$ is $2d_{max}$.

In the method in related art, GUI (Graphical User Interface) is first displayed on a display screen to prompt a user to keep a finger still. Thereafter, in the method in related art, a surface of the finger is imaged, and the first image data is generated and selected as the first candidate.

Subsequently, in the method in related art, a message prompting left rotation is displayed on the display screen, and detection is made as to whether the finger is actually rotated. When the amount of rotation reaches the limit value, the surface of the finger is imaged, and the second image data is generated and selected as the second candidate.

Subsequently, in the method in related art, a message prompting right rotation is displayed on the display screen, and detection is made as to whether the finger is actually rotated. When the amount of rotation reaches the limit value, in the method in related art, the surface of the finger is imaged, and the third image data is generated and selected as the third candidate.

As described above, at this moment, the user rotates the finger on its axis to the right or left in such an awkward way that the user is not accustomed to under the instruction given by the GUI of the application. If the order according to which the finger is to be moved to the right or left is predetermined, the order makes the operation more complicated, and further, some users may have a difficulty in moving the finger to a certain direction. Such operations placing an extremely heavy burden on the user may act as a barrier to usage.

Therefore, in the vein authentication apparatus and the template registration method according to each embodiment of the present invention as described below, less movement is forced to a user, and the GUI and the registration processing do not operate with each other. And information used for the registration is extracted from free movement of the user.

In the below explanation, an exemplary case will be explained where three template data are obtained. However, even when three or more template data are obtained, in the vein authentication apparatus and the template registration method according to each embodiment of the present invention, the processing can be performed in the same manner.

First Embodiment

Overview of Template Registration Method According to the Present Embodiment

Figure 2:
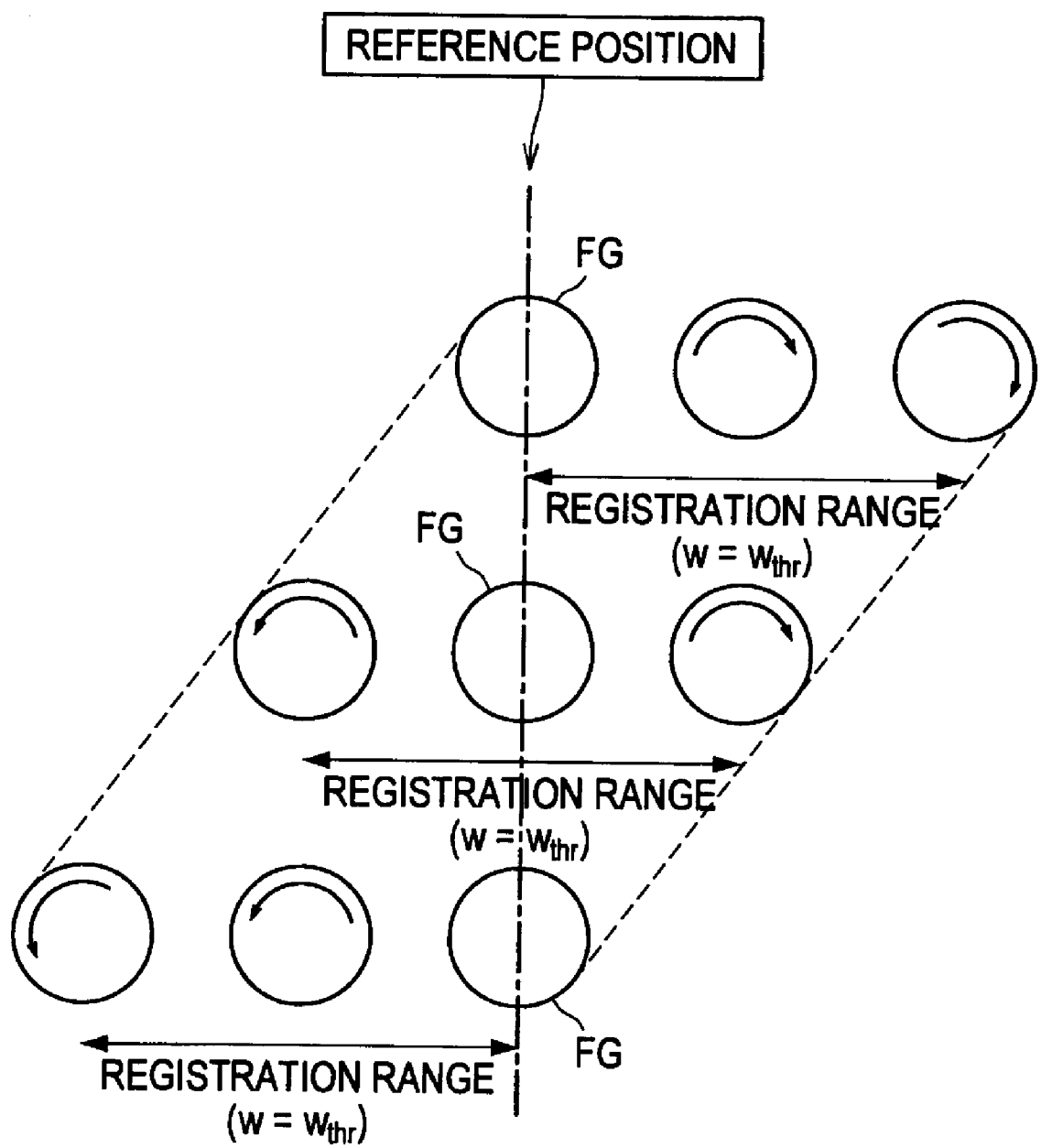
FIG. 2 is an explanatory diagram for illustrating the overview of the template registration method according to the embodiment.
Figure 3A:
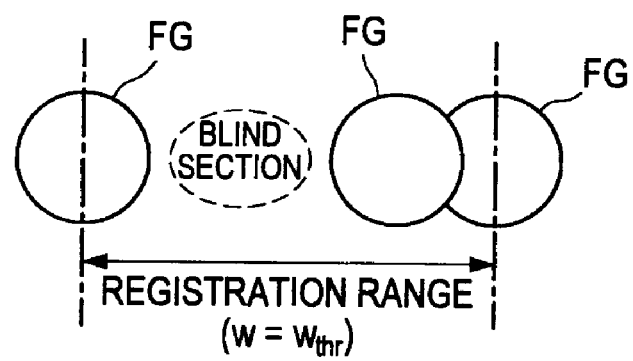
FIG. 3A is an explanatory diagram for illustrating the overview of the template registration method.
Figure 3B:
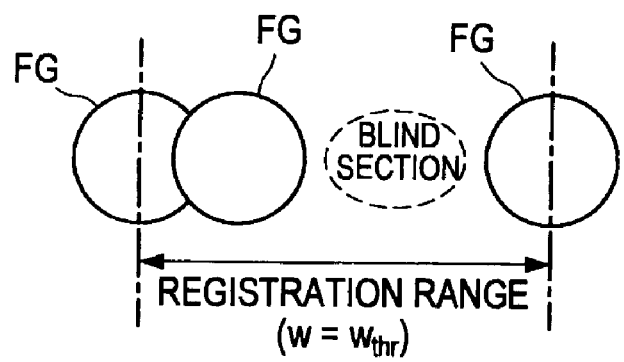
FIG. 3B is an explanatory diagram for illustrating the overview of the template registration method.

An overview of the template registration method according to the first embodiment of the present invention will be hereinafter described with reference to FIG. 1A to FIG. 3B. FIG. 1A to FIG. 2 are explanatory diagrams for illustrating the overview of the template registration method according to the present embodiment. FIG. 3A and FIG. 3B are explanatory diagrams for illustrating the overview of the template registration method.

As shown in FIG. 1A, in the template registration method according to the present embodiment, a finger surface FG placed above a light source unit LS of a vein authentication apparatus 10 is imaged with an imaging element Cam, so that a vein pattern is extracted. During the imaging, a user rotates a finger on its axis in a longitudinal direction as rotational axis with the axis being almost fixed. As a result, the finger of the user stays in proximity to the light source LS without moving in parallel.

Figure 1B:
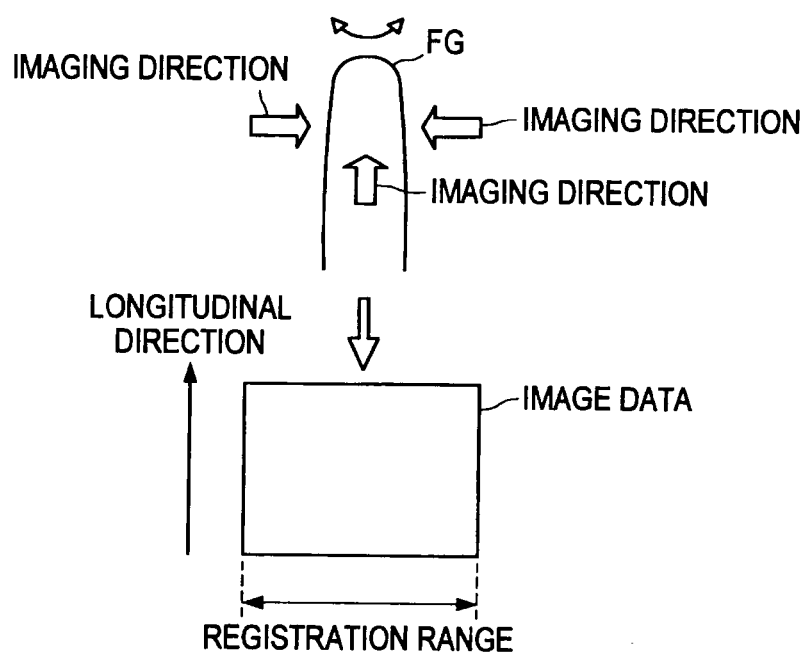
FIG. 1B is an explanatory diagram for illustrating the overview of the template registration method according to the embodiment.

When the finger is imaged in this state, the finger as imaged object is imaged from various directions as shown in FIG. 1B. As a result, such image data are obtained that has a predetermined expanse in the widthwise direction and a substantially constant length in the longitudinal direction. The width of this image data is a registration range that is to be registered as a template.

Next, how the finger is rotated in the template registration method according to the present embodiment will be explained with reference to FIG. 2. In the figures shown below, in a state where all the rotational axes are almost fixed, an amount of parallel movement of an image appearing in an imaging range (in other words, a length of an arc corresponding to rotation) is shown as the movement of the finger. It should be noted that the figures do not indicate that the finger itself moves in parallel.

In the template registration method according to the present embodiment, it is desirable to store a history of imaging in association with user's movement. In this example, even though a finger in a stationary state is to be captured at first, positional shifts of the finger caused by free movement of the finger (the user) are thereafter captured on the basis of the reference image obtained with respect to the finger in the stationary state, and the positions thereof are stored as a history. It should be noted that not all of the positional shifts should be stored as the history. The stored history may be updated only when there occurs a positional shift which causes the registration range to be expanded.

Therefore in contrast to the method in related art, as long as the registration range can be covered, the finger may be rotated to the right and left from the reference position in which the finger is in the stationary state, or may be rotated in one direction, i.e., either to the right or left, from the reference position in which the finger is the stationary state, as shown in FIG. 2.

With this method, even when it is difficult to rotate a finger either to the right or left, the template can be registered by rotating the finger only in one direction. The template registration method according to the present embodiment does not force the rotational direction to the user in conjunction with the of a GUI, and establishes a mechanism for allowing a user to register the template by freely rotating a finger while seeing a screen image showing a registration scene.

Next, the method for storing the history of the positional shifts will be explained with reference to FIG. 3A and FIG. 3B.

In the method in related art, the right and left limit positions are set in conjunction with a GUI. By holding a substantially center position, the right limit position, and the left limit position, the three types of template data are clearly shifted positionally from each other so that the registration range can be evenly covered.

In the method according to the present embodiment, however, the right and left limit positions are not set in conjunction with the GUI. Therefore, while positional shift data changes from time to time, the history is to be updated only when a positional shift occurs in such a direction that the registration range is expanded. Further, at that occasion, it is important how to select a central position (which does not necessarily serve as a reference) interposed between the right and left limit positions.

In other words, when a center is selected incorrectly, the template data includes a deviation either to the right or left as shown in FIG. 3A and FIG. 3B. Therefore, the arrangement positions of the template data are uneven, and the template data has a vacant position called a blind section. When a plurality of templates as shown in FIG. 3A and FIG. 3B are registered, there is a possibility that a user may not be authenticated when a vein pattern shifted to a direction opposite to the deviation is presented.

In view of the above circumstances, in the template registration method according to the present embodiment, the history of the vein pattern imaged and extracted is stored in accordance with the number of registered templates so as to be able to evenly cover the registration range, and the history is used for the template data.

<Configuration of Vein Authentication Apparatus>

Next, the configuration of the vein authentication apparatus 10 will be described in detail with reference to FIG. 4. FIG. 4 is a block diagram for illustrating the configuration of the vein authentication apparatus according to the present embodiment.

For example, as shown in FIG. 4, the vein authentication apparatus 10 according to the present embodiment includes a light source unit 101, an imaging unit 103, an imaging control unit 105. The vein authentication apparatus 10 according to the present embodiment further includes a vein pattern extraction unit 107, a rotation amount calculation unit 109, a registration information selection unit 111, a registration information compression unit 113, a template registration unit 115, a vein pattern authentication unit 117, and a memory unit 119.

The light source unit 101 emits a near infrared light having a predetermined wavelength band to a body surface (for example, finger surface) FG. The near infrared light is highly penetrative through body's tissues but is absorbed by hemoglobin (reduced hemoglobin) in the blood. Therefore, when the near infrared light is emitted to a finger, a palm, and the back of a hand, the vein distributed in the finger, the palm, and the back of the hand appear as a shadow in an image. The shadow of the vein appearing in the image is called a vein pattern. In order to favorably image the vein pattern, the light source unit 101 such as a light emitting diode emits a near infrared light having a wavelength of about 600 nm to 1300 nm, preferably 700 nm to 900 nm.

When the wavelength of the near infrared light emitted by the light source unit 101 is less than 600 nm or more than 1300 nm, the rate of the near infrared light absorbed by the hemoglobin in blood decreases, which makes it difficult to obtain a good vein pattern. When the wavelength of the near infrared light emitted by the light source unit 101 is about 700 nm to 900 nm, the near infrared light is specifically absorbed by both of deoxygenated hemoglobin and oxygenated hemoglobin, which brings a good vein pattern.

Instead of using the light source such as the light emitting diode having the wavelength band as described above, it is possible to use a combination of a light emitting diode capable of emitting a light including the above wavelength band and a filter optically restricting the band of the emitted light.

The near infrared light emitted from the light source unit 101 propagates toward the finger surface FG, and enters as a direct light the inside of the living body through the side surface thereof. The human body is a good scatterer of the near infrared light, and therefore, the direct light entered the living body propagates while scattering in all directions. The near infrared light being transmitted through the living body enters an optical element of the imaging unit 103.

The imaging unit 103 is constituted by an optical system constituted by an optical element such as a lens and an imaging element such as a CCD (Charge Coupled Devices) and a CMOS (Complementary Metal Oxide Semiconductor).

The optical system constituting the imaging unit 103 includes one or a plurality of optical elements and one or a plurality of imaging elements. The optical system of the imaging unit 103 according to the present embodiment may be dedicated for the vein authentication processing. Alternatively, an existing optical system may be used as the imaging system for the vein imaging. For example, when the vein authentication apparatus 10 according to the present embodiment is implemented in a portable device such as a portable telephone, an optical system already implemented in the portable apparatus can be used as the optical system for the vein imaging.

A human skin is known to be constituted by three layers, i.e., an epidermis layer, a dermis layer, and a hypodermis layer. A vein layer in which veins are present is in the dermis layer. The dermis layer is in a depth of about 0.1 mm to 0.3 mm from a finger surface, and has a thickness of about 2 mm to 3 mm. Therefore, when a focal position of the optical element such as a lens is set to a position at which the dermis layer is present (for example, in a depth of about 1.5 mm to 2.0 mm from the finger surface), a light penetrating through the vein layer can be effectively collected.

The light having penetrating through the vein layer, which is collected by the optical element, is focused on the imaging element to be converted into imaged vein data.

The imaging control unit 105 is constituted by, for example, a CPU (Central Processing Unit), a ROM (Read Only Memory), a RAM (Random Access Memory) and the like. At every predetermined time interval, the imaging control unit 105 controls the light source unit 101 and the imaging unit 103 and generates a plurality image data. The time interval during which the finger surface FG is imaged can be set to any value in accordance with a processing performance and the like of the vein authentication apparatus 10 according to the present embodiment.

The imaging control unit 105 outputs the image data generated by the imaging element to the later-described vein pattern extraction unit 107. The imaging control unit 105 may record the obtained image data to the later-described memory unit 119. When the obtained image data is recorded to the memory unit 119, the imaging control unit 105 may associate the generated image data with an imaging date, an imaging time, and the like. The generated image data may be an RGB (Red-Green-Blue) signal. Alternatively the generated image data may be imaging data in other colors or gray scale image data or the like.

The imaging unit 103 according to the present embodiment may be a so-called transmissive imaging unit that images a light which is emitted by the light source unit 101 and which is transmitted through the inside of the finger. Alternatively, the imaging unit 103 may be a so-called reflective imaging unit imaging a reflection light of the near infrared light reflected in the inside of the finger.

The vein pattern extraction unit 107 is constituted by, for example, a CPU, a ROM, and a RAM and the like. The vein pattern extraction unit 107 has the functions for performing pre-processing for the vein pattern extraction on the near infrared light image data transferred from the imaging control unit 105, and for performing the vein pattern extraction on the near infrared light image data, and for performing a post-processing for the vein pattern extraction on the near infrared light image data.

Herein, the above pre-processing for the vein pattern extraction includes, for example, processing for detecting an outline of a finger from the image data and for determining at which position of the image data the finger is located, and the processing for rotating the image data within a plane using the detected outline of the finger and for correcting the angle of the image data (angle of the photographed image).

The above extraction of the vein pattern is performed by applying a difference filter to the image data in which the outline has been detected and the angle has been corrected. In a portion where there is a large difference between a target pixel and pixels around the target pixel, the difference filter outputs a larger value as an output value. In other words, the difference filter is a filter for emphasizing lines and edges in an image by performing calculation using a difference in a gradation value between a target pixel and pixels around the target pixel.

In general, where a filter processing with a filter h(x,y) is performed on image data u(x,y) having a lattice point (x,y) on a two-dimensional plane, image data v(x,y) is generated as shown in Formula 1 below. In Formula 1 shown below, '*' represents a convolution integral.

$$v(x, y) = u(x, y) * h(x, y) \quad \text{(Formula 1)}$$
$$= \sum_{m_1} \sum_{m_2} h(m_1, m_2) u(x - m_1, y - m_2)$$
$$= \sum_{m_1} \sum_{m_2} u(m_1, m_2) h(x - m_1, y - m_2)$$

In the extraction of the vein pattern according to the present embodiment, a differential filter such as one-dimensional space differential filter and two-dimensional space differential filter may be used as the above difference filter. The one-dimensional space differential filter calculates a difference in a gradation value between a target pixel and pixels adjacent in the lateral direction and between the target pixel and pixels adjacent in the longitudinal direction. The two-dimensional space differential filter extracts a portion where the difference in the gradation value of the target pixel varies much.

For example, a Log (Laplacian of Gaussian) filter shown below can be used as the above two-dimensional space differential filter. A Log filer (Formula 3) is represented by a secondary differentiation of Gaussian filter (Formula 2), i.e., a smoothing filter using the Gaussian function. In Formula 2 shown below, σ denotes a standard deviation of the Gaussian function, and is a variable for representing the degree of smoothing of the Gaussian filter. In the below Formula 3, σ denotes a parameter for representing a standard deviation of the Gaussian function in the same manner as Formula 2, and an output value when performing the Log filter processing can be changed by changing the value of σ.

$$h_{gauss}(x, y) = \frac{1}{2\pi\sigma^2} \exp\left\{-\frac{(x^2 + y^2)}{2\sigma^2}\right\} \quad \text{Formula 2}$$

$$h_{Log}(x, y) = \nabla^2 \cdot h_{gauss}(x, y) \quad \text{Formula 3}$$
$$= \left(\frac{\partial^2}{\partial x^2} + \frac{\partial^2}{\partial y^2}\right) h_{gauss}$$
$$= \frac{(x^2 + y^2 - 2\sigma^2)}{2\pi\sigma^6} \exp\left\{-\frac{(x^2 + y^2)}{2\sigma^2}\right\}$$

The above post-processing for the vein pattern extraction includes, for example, a threshold processing, a binarization processing, and a thinning processing, which are performed on the image data to which the difference filter has already been applied. After these processings, a skeleton of the vein pattern can be extracted.

The vein pattern extraction unit 107 transfers the thus extracted vein pattern and skeleton to the rotation amount calculation unit 109, the vein pattern authentication unit 117, and the like, which are explained later. Further, the vein pattern extraction unit 107 may store the extracted vein pattern and skeleton in the later-described memory unit 119. The vein pattern extraction unit 107 may store parameters generated when the above processings are performed and intermediate data of processings and the like in the memory unit 119.

The rotation amount calculation unit 109 is constituted by, for example, a CPU, a ROM, a RAM, and the like. The rotation amount calculation unit 109 first selects one vein pattern from among the plurality of vein patterns transferred from the vein pattern extraction unit 107. This vein pattern is preferably set as the first vein pattern in which the finger in the stationary state is imaged. Next, the rotation amount calculation unit 109 calculates a rotational direction and the amount of rotation of a finger associated with a rotational movement of each of the extracted vein pattern, by using the imaging range of the selected vein pattern as a reference. Various methods can be used for calculating the rotational direction and the amount of rotation. For example, a following method can be used.

For example, the rotational direction and the amount of rotation can be obtained by calculating a correlation coefficient between the vein pattern selected as the reference and the vein pattern other than the selected vein pattern.

The correlation coefficient is defined by Formula 4 shown below, and is a statistical index representing the degree of similarity between two data f1 and f2. The correlation coefficient is a real number from −1 to 1. When the correlation coefficient has a value close to 1, two data are similar. When the correlation coefficient has a value close to 0, two data are not similar. When the correlation coefficient has a value close to −1, two data have values of opposite sign.

In this specification, f1 and f2 are data representing vein patterns, and have an image size of M rows by N columns. It is assumed that a pixel in each vein pattern is represented as (m, n).

$$S(f1, f2) = \frac{\sum_{m=0}^{M-1} \sum_{n=0}^{N-1} f1(m, n) \cdot f2(m, n)}{\sqrt{\left\{\sum_{m=0}^{M-1} \sum_{n=0}^{N-1} f1(m, n)^2\right\}} \sqrt{\left\{\sum_{m=0}^{M-1} \sum_{n=0}^{N-1} f2(m, n)^2\right\}}} \quad \text{Formula 4}$$

Figure 5:
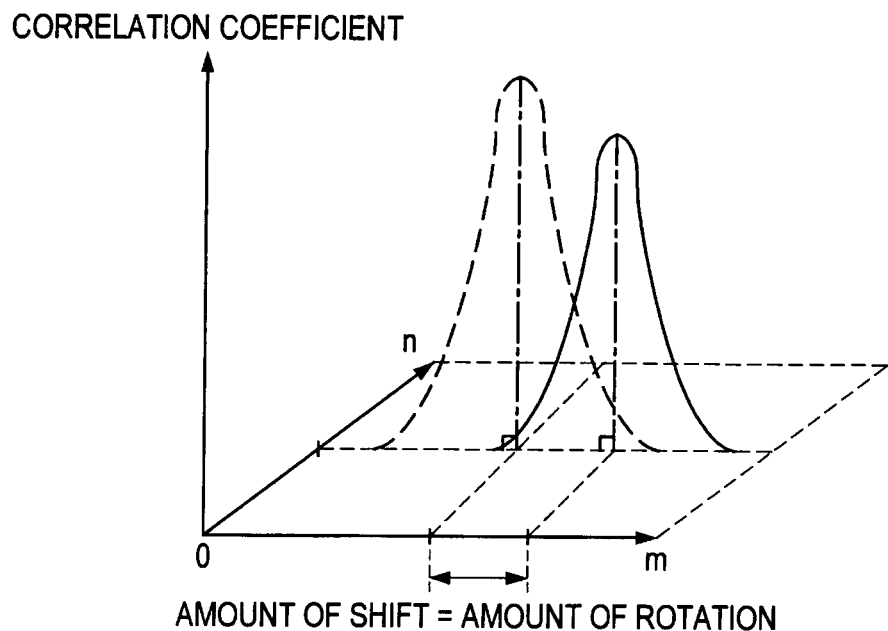
FIG. 5 is an explanatory diagram for illustrating a calculation of a rotational direction and an amount of rotation.

Herein, when the two data f1 and f2 are completely the same, the correlation coefficient therebetween has a value of 1, and its peak position is nearly in the center of an mn plane as shown in FIG. 5. Therefore, when a correlation coefficient is calculated as the vein pattern selected by using both of the data f1 and f2 as the reference, the correlation coefficient therebetween is 1, and its peak position is a reference peak position used to calculate the rotational direction and the amount of rotation.

Next, the correlation coefficient is calculated where the vein pattern selected as the reference is f1 and the vein patterns other than the selected vein pattern are f2. When the calculated correlation coefficient is equal to or more than a predetermined threshold value, it is highly possible that the vein patterns other than the selected vein pattern is an image obtained with respect to a finger actually rotated. Further, as shown by a solid line in FIG. 5, a direction of a shift of the calculated peak position from the reference peak position corresponds to the rotational direction, and the amount of shift at the peak position corresponds to the amount of rotation.

The rotation amount calculation unit 109 transfers the calculated rotational direction, the calculated amount of rotation, and the corresponding vein pattern to the later-described registration information selection unit 111. The rotation amount calculation unit 109 may record the calculated rotational direction the calculated amount of rotation, by associating them with the corresponding vein pattern, to the later-described memory unit 119.

The registration information selection unit 111 is constituted by, for example, a CPU, a ROM, a RAM, and the like. The registration information selection unit 111 calculates a shift width of the imaging range on the basis of the rotational direction and the amount of rotation having been transferred from the rotation amount calculation unit 109, and determines whether the shift width of the imaging range is equal to or more than a predetermined threshold value. Where the generated vein pattern has a size (magnitude) of, for example, 160 pixels long and 60 pixels wide. the above threshold may be set to, for example, about 6 pixels, i.e., about 10% of the pixels representing the imaging range of the vein pattern serving as the reference. This threshold value of the shift width of the imaging range is the registration range ($w=w_{thr}$) of the template including rotational shift.

When the shift width of the imaging range is equal to or more than the predetermined threshold value as a result of determination, the registration information selection unit 111 selects all of the extracted vein patterns as registration information.

When the shift width of the imaging range is less than the predetermined threshold value as a result of determination, the registration information selection unit 111 continues the determination for the plurality of vein patterns successively transferred, until the shift width becomes equal to or more than the predetermined threshold value. More specifically, the registration information selection unit 111 stores the vein patterns located at both ends of the imaging range among the transferred vein pattern. Further, the registration information selection unit 111 selects a vein pattern spaced apart from adjacent vein patterns by almost the same distance from among the plurality of vein patterns present between the vein patterns located at both ends.

The registration information selection unit 111 may reconsider the content of the vein patterns already registered as the template using the authenticated vein pattern which is transferred from the later-described vein pattern authentication unit 117, and may re-select registration information using the already registered vein pattern and the authenticated vein pattern.

The selection processing of the registration information performed by the registration information selection unit 111 will be explained in detail again later.

When the registration information selection unit 111 obtains a determination result indicating that a shift width is determined to be equal to or more than the predetermined threshold value, the registration information selection unit 111 sorts the registration information, which is selected at the moment, in ascending order from the registration information in which the shift amount has the smallest absolute value. For example, a case will be considered where registration information #1 having a shift amount of +3, registration information #2 having a shift amount of ±0, and registration information #3 having a shift amount of −2 are selected when the shift width is equal to or more than the predetermined threshold value. Herein, the numbers #1, #2 and #3 represent the order in which the registration information is selected. In this case, the registration information selection unit 111 sorts the above three pieces of registration information in the following order: the registration information #2 (absolute value of shift amount: 0), the registration information #3 (absolute value of shift amount: 2), and the registration information #1 (absolute value of shift amount: 3).

In the above-explained example, registration information having a positive shift amount and registration information having a negative value coexist across the reference position (i.e., shift amount±0). Even when there is only registration information having a positive shift or registration information having a negative shift, the registration information selection unit 111 sorts the registration information in ascending order from the registration information in which the shift amount has the smallest absolute value in the same manner as described above.

The order in which the registration information is sorted in the manner described above serves as the order for collating templates when the vein authentication apparatus 10 performs the authentication processing on the vein pattern.

The registration information selection unit 111 transfers the registration information sorted according to the above method to the registration information compression unit 113 with the sort order being preserved.

The registration information compression unit 113 is constituted by, for example, a CPU, a ROM, a RAM, and the like. The registration information compression unit 113 compresses the registration information, which is transferred from the registration information selection unit 111, on the basis of a predetermined method. At this occasion, the registration information compression unit 113 performs, for the plurality of pieces of transferred registration information, the compression processing of each registration information such that an amount of data of the first registration information is larger than that of the second and subsequent registration information. In other words, the registration information compression unit 113 performs the compression processing of each registration information such that a compression rate of the first registration information is not lower than that of the second and subsequent registration information.

The amount of data and the compression rate for compressing the registration information can be set to any value in accordance with the size and the like of an area for storing the compressed registration information as templates (which may also be hereinafter referred to as template storage area). In the below explanation, it is assumed that an area of 512 bytes is reserved as the template registration area, and a procedure for determining the amount of data and the like of the registration information will be hereinafter explained with reference to FIG. 6.

First, the registration information compression unit 113 reserves an area for storing information used when templates such as parameters are used (parameter storage area) in the template storage area. Subsequently, the registration information compression unit 113 determines an amount of data having a relatively small value, which can be set without affecting the authentication processing, in consideration of the size of the template storage area except for the area reserved for the parameter storage area. The determined amount of data is the amount of compressed data of the second and subsequent registration information. The amount of data of the first registration information is the amount of data except for the amount of data for the area of the parameter storage area and the area in which the second and subsequent compressed registration information are present.

Figure 6:
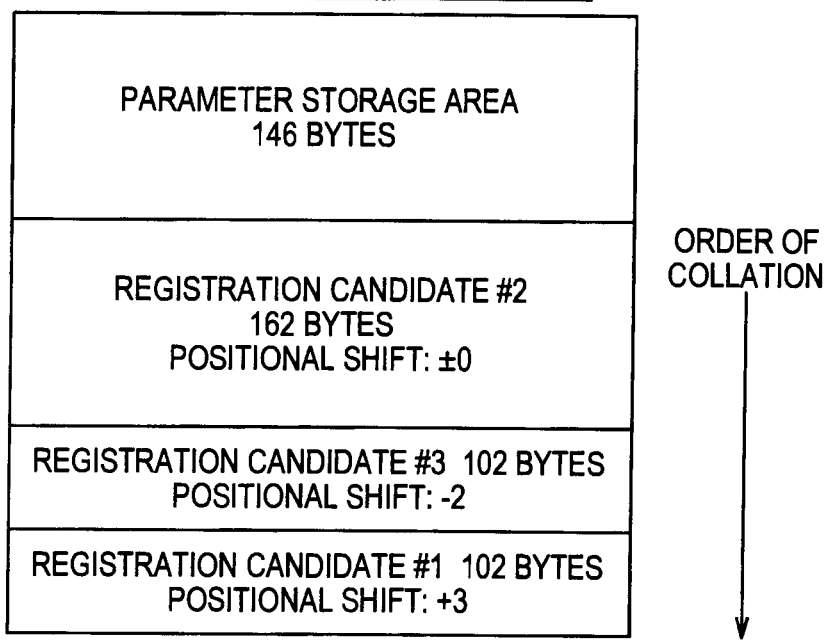
FIG. 6 is an explanatory diagram for illustrating a selection processing of registration information performed by the vein authentication apparatus according to the embodiment.

In the example shown in FIG. 6, for example, the template storage area is 512 bytes, and 146 bytes are reserved as the parameter storage area. 102 bytes are respectively reserved as the amount of compressed data of the second and subsequent registration information. The remaining 162 bytes are reserved as the amount of compressed data of the first registration information.

With this compression processing, the largest data storage area can be reserved for the registration information corresponding to the template first collated during the authentication processing among the registration information stored as templates.

In present method, the plurality of pieces of registration information having different amounts of positional shift are registered as templates, and the registration information is selected in such a manner that the imaging range of each template overlaps with each other in order to eliminate a blind section. The registration information in which the shift amount has the smallest absolute value is information located nearest to the reference position (i.e., the shift amount±0), but this registration information includes a portion of other registration information located to the left and right of the reference position. Therefore, when the registration information in which the shift amount has the smallest absolute value is caused to have a large amount of data, the registration information having more information can have almost the same amount of information as the non-compressed registration information, so that it is possible to increase the probability that the authentication is successfully performed with the first collated template. Therefore, the authentication speed and the convenience can be improved by changing the compression rates of the registration information as described above.

Figure 7:
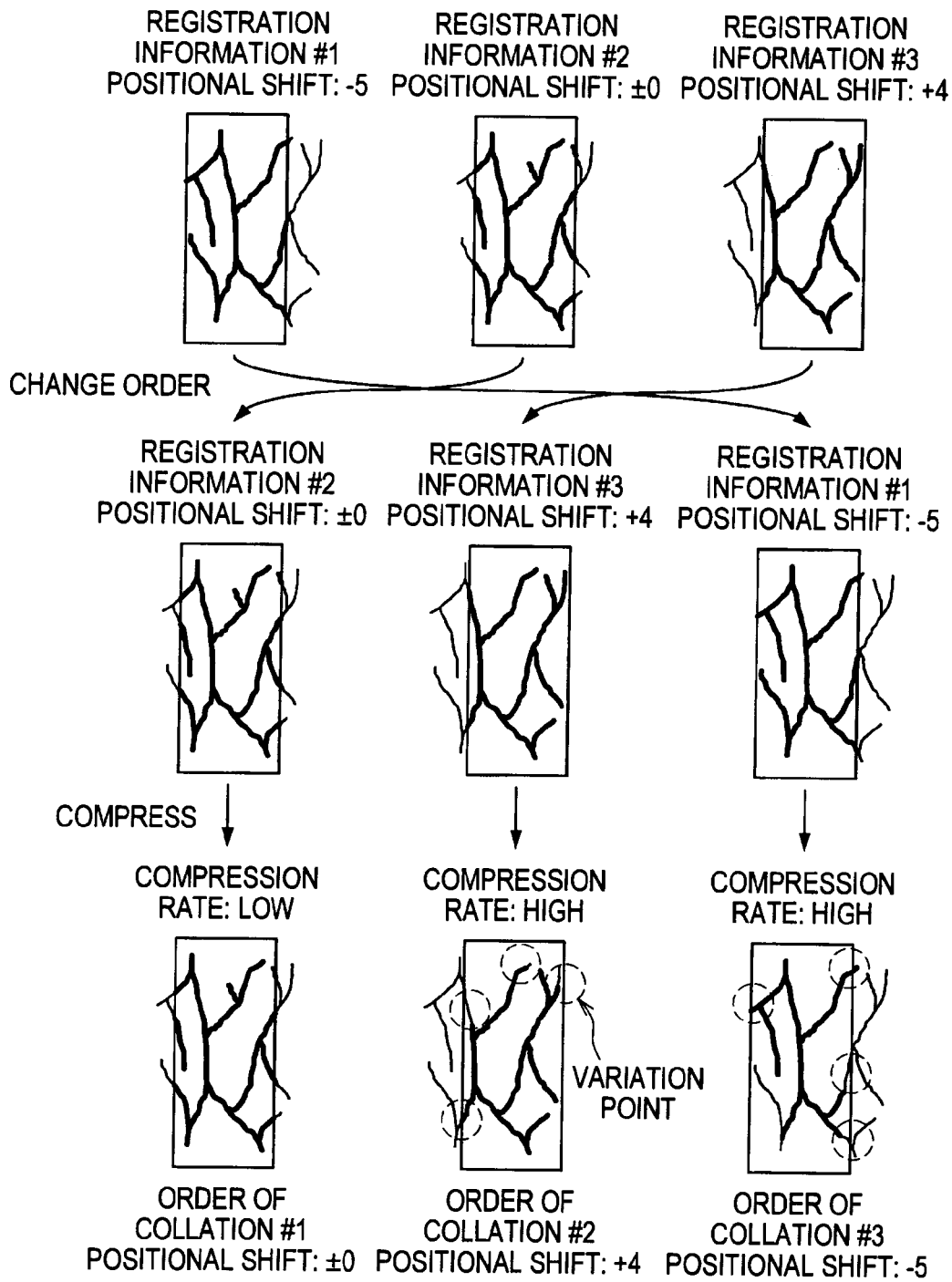
FIG. 7 is an explanatory diagram for illustrating a selection processing of registration information performed by the vein authentication apparatus according to the embodiment.

FIG. 7 is an explanatory diagram for illustrating an exemplary compression of actual registration information. In FIG. 7, a rectangular box represents an imaging range, and a portion indicated by a thick line represents an extracted vein portion. As is evident from the three types of registration information located in the upper row of FIG. 7, only a portion of an entire vein pattern is imaged for each of the registration information. First, the registration information selection unit 111 sorts the registration information as shown in the middle row of FIG. 7. Subsequently, the registration information compression unit 113 performs the compression processing on the registration information. Differentiation of the amount of data can be performed by considering how much information about portions corresponding to variation points is to be included in a template as shown in the lower row of FIG. 7. Herein, the variation point means, e.g., a branching point of a line representing a vein and a point at which a slope of a line changes. The compression rate may be increased by omitting the ends of the lines from a template as shown in the registration information located in the center of the lower row of FIG. 7 and omitting one of branch veins branching at a branching point from a template as shown in the registration information located at the right end of the lower row of FIG. 7.

The template registration unit 115 will be described with reference back to FIG. 4. The template registration unit 115 is constituted by, for example, a CPU, a ROM, a RAM, and the like. The template registration unit 115 registers the registration information transferred from the registration information compression unit 113 (i.e., the vein pattern) as a template to the later-described memory unit 119. When the registration vein pattern is registered, not only the vein pattern but also other data for identifying an individual having the vein pattern (for example, finger print data, face image data, iris data, and voiceprint data) may be registered in association with the vein pattern. Further, the registration vein pattern to be registered as the template may have header information according to a standard such as CBEFF (Common Biometric Exchange File Format Framework).

The vein pattern authentication unit 117 is constituted by, for example, a CPU, a ROM, a RAM, and the like. The vein pattern authentication unit 117 authenticates the generated vein pattern on the basis of the already recorded template of the vein pattern and the vein pattern generated by the vein pattern extraction unit 107. The vein pattern authentication unit 117 requests the later-described memory unit 119 to disclose the template, and compares the obtained template with the vein pattern transferred from the vein pattern extraction unit 107. The template and the transferred vein pattern can be compared on the basis of, for example, the correlation coefficient calculated by Formula 4 shown above. When the template and the transferred vein pattern are determined to be similar to each other as a result of comparison, the vein pattern authentication unit 117 determines that the transferred vein pattern has been successfully authenticated. When the template and the transferred vein pattern are determined not to be similar to each other, the vein pattern authentication unit 117 determines that the authentication has failed.

Alternatively, the vein pattern authentication unit 117 may record the authentication result as an authentication history to the memory unit 119 in association with an authentication time and the like. When such authentication history is generated, it is possible to know who requested the authentication of the vein pattern, when the request is made, who used the vein authentication apparatus 10, and when the vein authentication apparatus 10 is used.

The vein pattern authentication unit 117 notifies the vein pattern successfully authenticated to the registration information selection unit 111, so that the vein pattern may be used to update the registration information.

The memory unit 119 stores the registration vein pattern whose registration is requested by the template registration unit 115 and other data associated with the registration vein pattern. Further, the memory unit 119 may store not only these data but also image data generated by the imaging control unit 105, the vein pattern extracted by the vein pattern extraction unit 107, and the like. Further, the memory unit 119 can store, as necessary, not only these data but various parameters and intermediate data or various databases, which are to be saved when the vein authentication apparatus 10 performs a certain processing. This memory unit 119 can be freely read and written by the imaging control unit 105, the vein pattern extraction unit 107, the rotation amount calculation unit 109, the registration information selection unit 111, the registration information compression unit 113, the template registration unit 115, and the vein pattern authentication unit 117.

Exemplary functions of the vein authentication apparatus 10 according to the present embodiment have been shown hereinabove. Each of the above constituent elements may be made with a generally-used member and circuit, or may be made with hardware dedicated for the purpose of each constituent element. Alternatively, all of the functions of the constituent elements may be performed by a CPU and the like. Therefore, the used configuration may be changed as necessary in accordance with the state of art at the time of carrying out the present embodiment.

It is possible to make a computer program for realizing the functions of the above-described vein authentication apparatus 10 according to the present embodiment, and the computer program can be implemented on a personal computer and the like. Further, a computer-readable recording medium storing such computer program can be provided. Examples of the recording medium include a magnetic disk, an optical disk, a magneto-optical disk, and a flash memory. Further, the above computer program may be distributed by, for example, a network, without using the recording medium.

<Details of Template Registration Method>

Next, the method for selecting the registration information performed by the registration information selection unit 111 of the vein authentication apparatus 10 according to the present embodiment will be described in detail with reference to FIG. 8 to FIG. 12.

For the sake of simplicity, a method for registering three vein patterns as registration information will be explained in the below. As described above, when the first stationary state is captured, the vein pattern serving as the reference is determined, and the first registration candidate is determined. Subsequently, when there is an input which causes the registration range to be expanded, the vein pattern corresponding to the input is stored (added to the history) as the registration candidate. Then, the range is further expanded, and the stored history is updated as long as the input is within the expected registration range ($w=w_{thr}$). Herein, although all of the history may be stored, the history is preferably updated in consideration of memory consumption and the like. Herein, three vein patterns are registered as templates. Therefore, the two vein patterns subsequent to the first vein pattern in which the stationary state is captured, are updated.

Figure 8:
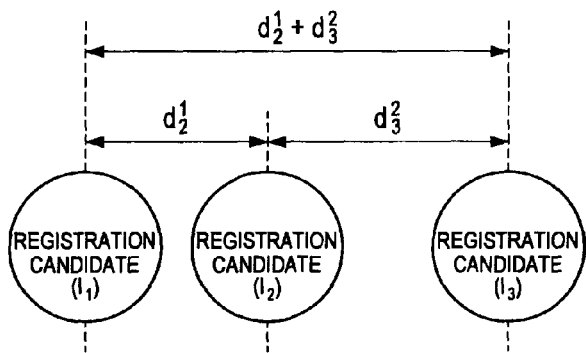
FIG. 8 is an explanatory diagram for illustrating a selection processing of registration information performed by the vein authentication apparatus according to the embodiment.

As shown in FIG. 8, registration data of the first vein pattern extracted first is denoted as $I_1$, and the amount of positional shift with respect to the registration data $I_1$ is denoted as $d_1^1$. In this case, $d_1^1=0$. Registration data of the two vein patterns subsequently extracted are denotes as $I_2$, $I_3$, respectively, and the amounts of positional shifts thereof with respect to $I_1$ is denoted as $d_2^1$, $d_3^1$, respectively.

Right after the stationary state is captured, the candidate for the registration information is only the first vein pattern. Therefore, the rotation amount calculation unit 109 measures a positional shift between data which is input every moment (vein pattern) and the first candidate data $I_1$. Further, the registration information selection unit 111 determines whether the vein pattern is to be added to the registration candidate on the basis of the result notified by the rotation amount calculation unit 109.

When the third vein pattern is added as the registration candidate ($I_3$), the rotation amount calculation unit 109 measures a positional shift between the third vein pattern and the registration candidates $I_1$ and $I_2$. When measuring the positional shift from $I_1$, the positional shift $d_3^1$ itself is stored. When measuring the positional shift from $I_2$, the rotation amount calculation unit 109 calculates $d_3^1$ by adding $d_2^1$ and $d_3^2$ on the basis of the amount of positional shift $d_2^1$ of the registration candidate $I_2$ with respect to $I_1$ and the amount of positional shift $d_3^2$ of the registration candidate $I_3$ with respect to $I_2$.

The positional shifts are not measured only from a peak position of a cross-correlation value (correlation coefficient), but the positional shift therebetween is employed only when peak values are similar to some degree. Therefore, with respect to which registration candidates the positional shift measurement values are employed depends on how a user himself moves a finger. In the present embodiment, up to three vein patterns are determined as registration candidates in a mechanical fashion, but after the three registration candidates are registered, two of the three registration candidates are updated in order to cover the expected registration range ($w=w_{thr}$).

Subsequently, the method for updating the two vein patterns will be explained in detail. In this case, the following two kinds of expected states are considered.

(A) Registration range is expanded to only one side
(B) Registration range is expanded to right and left directions

[Registration Range is Expanded to Only One Side]

First, (A) a case where the registration range is expanded to only one side will be explained in detail with reference to FIG. 9 to FIG. 11B. In this case, for example, as shown in the upper row of FIG. 9, the first vein pattern in which the stationary state is captured is always at the edge of the registration range, and the second and third registration candidates of the vein patterns are determined in a direction away from the first vein pattern.

Figure 9:
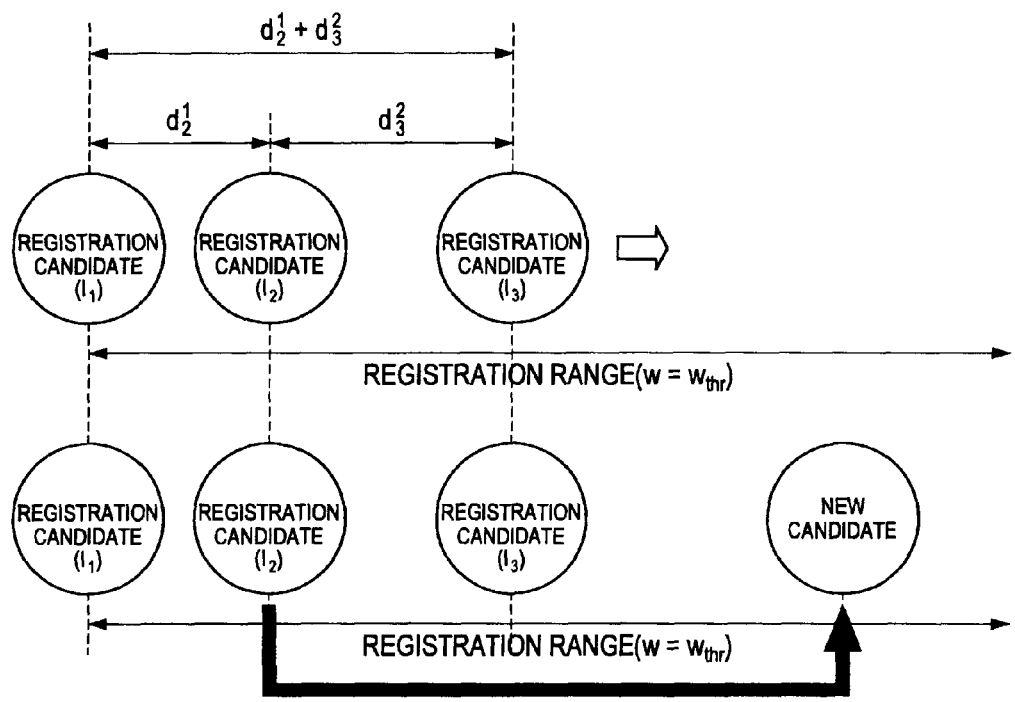
FIG. 9 is an explanatory diagram for illustrating a selection processing of registration information performed by the vein authentication apparatus according to the embodiment.

Herein, the registration range determined by the first vain pattern to the third vein pattern is narrower than the threshold value of the registration range ($w=w_{thr}$) as shown in the upper row of FIG. 9. Therefore, when the fourth and subsequent new candidates are input as shown in the lower row of FIG. 9, it is to be considered that the registration candidates are to be located at an equal distance from each other. In this case, while the registration information selection unit 111 holds the registration candidates located at both ends of the registration range defined by the plurality of registration candidates for vein patterns, the registration information selection unit 111 selects a registration candidate located in a position from which distances to adjacent registration candidates are close to be equal from among the registration candidates existing on the inner side. In other words, in the example shown in the lower row of FIG. 9, the content of the registration candidate $I_2$ is updated to the content of the new candidate among the registration candidates $I_1$ to $I_3$ currently being kept.

Figure 10A:
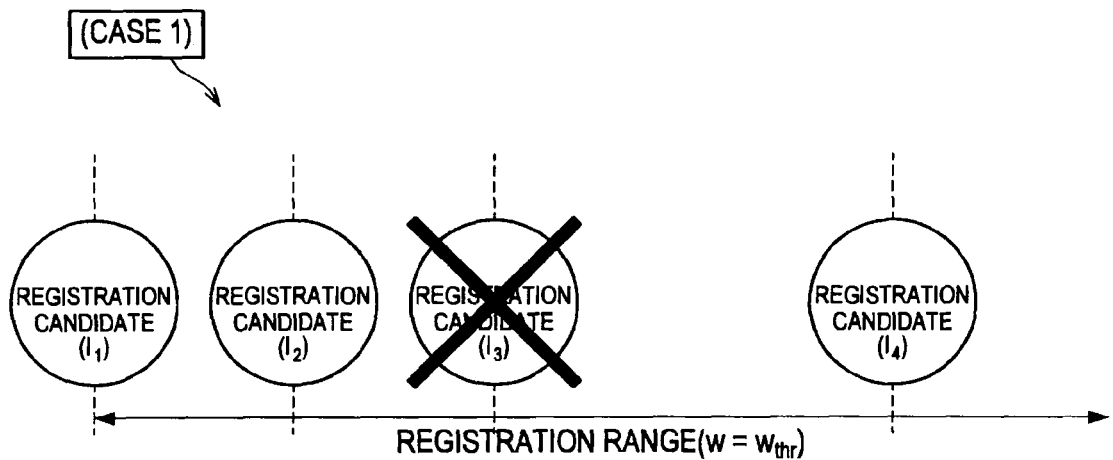
FIG. 10A is an explanatory diagram for illustrating a selection processing of registration information performed by the vein authentication apparatus according to the embodiment.
Figure 10B:
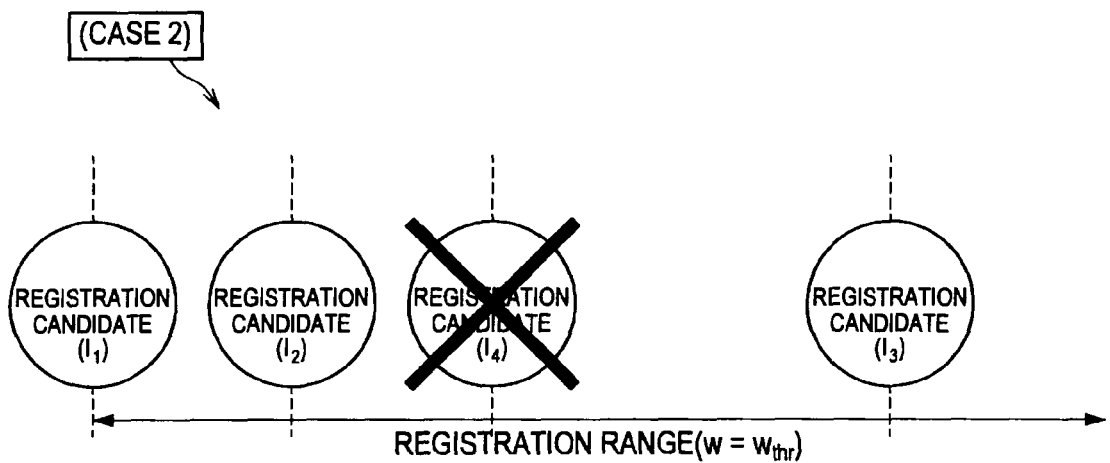
FIG. 10B is an explanatory diagram for illustrating a selection processing of registration information performed by the vein authentication apparatus according to the embodiment.

Considering that the registration candidates are located at an equal distance from each other as described above, when comparing between the situations in which the registration range is covered by selecting of the registration candidates, there may be a case where the selection of the registration candidates results in an unfavorable registration example as shown in FIG. 3A and FIG. 3B. In other words, as shown in FIG. 10A (case 1), when the history of $I_3$ is erased and $I_1$, $I_2$, $I_4$ are selected as the registration candidates, a blind section is generated between $I_2$ and $I_4$, which is unfavorable. Alternatively, as shown in FIG. 10B (case 2), when the history of $I_4$ is erased and $I_1$, $I_2$, $I_3$ are selected as the registration candidates, a blind section is generated between $I_2$ and $I_3$, which is unfavorable.

In view of such circumstances, when a new candidate is $I_x$, the registration information selection unit 111 calculates the amount of positional shift between the new input candidate and each registration candidate, and closely examines each registration candidate so that the registration candidates are located at an equal distance within the registration range.

Figure 11A:
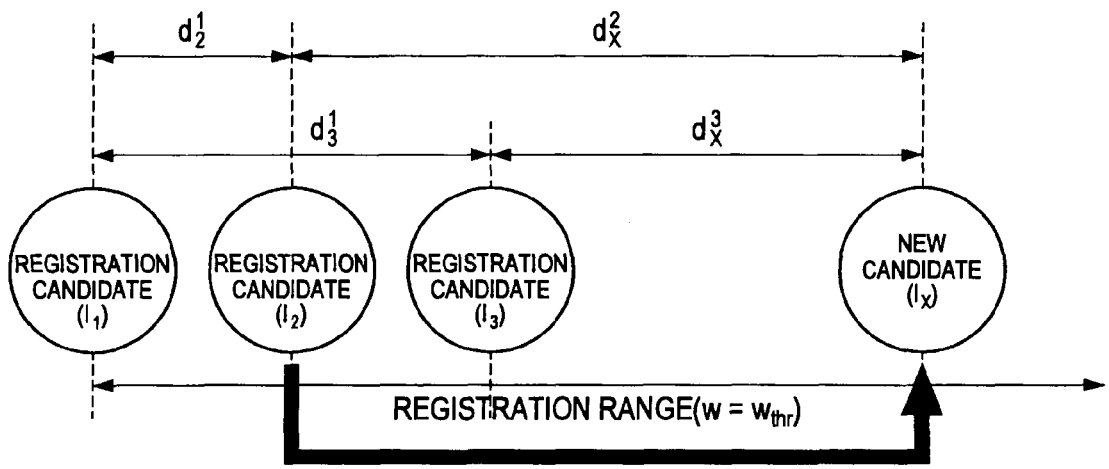
FIG. 11A is an explanatory diagram for illustrating a selection processing of registration information performed by the vein authentication apparatus according to the embodiment.

As shown in FIG. 11A, first, the rotation amount calculation unit 109 calculates the amount of positional shift between a new candidate data $I_x$ and each registration candidate, and notifies the amount of positional shift to the registration information selection unit 111. While the registration information selection unit 111 holds the registration candidate $I_1$ and the new candidate $I_x$, which are located at both ends, among the four registration candidates, the registration information selection unit 111 determines which of the registration candidate $I_2$ and the registration candidate $I_3$ is to be selected, which are located between the registration candidate $I_1$ and the new candidate $I_x$.

First, the registration information selection unit 111 examines the registration candidate $I_2$. When the registration candidate $I_2$ is kept as the main registration candidate, whether the candidates are located at an equal distance within the registration range can be determined on the basis of a difference of the amount of positional shift from $I_2$, $\Delta d_2$. As shown in FIG. 11A, the difference of the amount of positional shift from $I_2$, $\Delta d_2$ can be expressed with Formula 5 shown below using the amounts of positional shifts from $I_2$, $d_2{}^1$ and $d_x{}^2$.

Similarly, the registration information selection unit 111 examines the registration candidate $I_3$ by calculating the difference of the amount of positional shift from $I_3$, $\Delta d_3$. In the registration information selection unit 111, the amount of positional shift from $I_3$, $\Delta d_3$ can be expressed as Formula 6 shown below using the amounts of positional shifts from $I_3$, $d_3{}^1$ and $d_x{}^3$.

$$\Delta d_2 = |d_2{}^1 - d_x{}^2| \quad \text{(Formula 5)}$$

$$\Delta d_3 = |d_3{}^1 - d_x{}^3| \quad \text{(Formula 6)}$$

The smaller the value of the calculated $\Delta d$ is, more closer to the center of the registration range the target registration candidate is located. Therefore, when the registration range is expanded to only one direction, a vein pattern with the smaller difference is to be kept as the registration candidate.

In other words, in the case shown in FIG. 11A, $\Delta d_3$ is smaller than $\Delta d_2$, and therefore, the registration information selection unit 111 updates the history of the registration candidate $I_2$, and newly selects the registration candidate $I_1$, the registration candidate $I_3$, and the new candidate $I_x$ as the registration candidates.

Further, in the example where the registration range is expanded to one direction, the registration candidates are to be updated when the new candidate further contributes to an even arrangement of the registration candidates even when the registration range is not expanded by the new candidate.

Figure 11B:
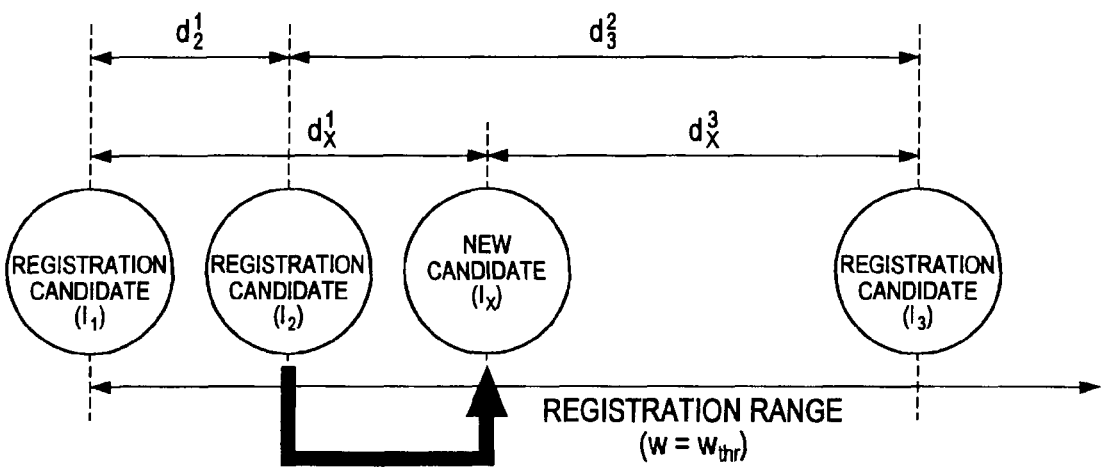
FIG. 11B is an explanatory diagram for illustrating a selection processing of registration information performed by the vein authentication apparatus according to the embodiment.

In other words, as shown in FIG. 11B, even if the already arranged registration range is not expanded by the new candidate, the registration candidate is updated when the registration candidates can be located at an more equal distance by making the new candidate a registration candidate. In the case shown in FIG. 11B, a distance between registration candidates adjacent to each other comes to be almost equal by holding the new candidate $I_x$ which is newly input rather than by storing the history of the registration candidate $I_2$. Therefore, the registration information selection unit 111 updates the history of the registration candidate $I_2$, and newly selects the registration candidate $I_1$, the registration candidate $I_3$, and the new candidate $I_x$ as the registration candidates.

[Registration Range is Expanded to Right and Left Directions]

Next, (B) a case where the registration range is expanded to the right and left directions will be explained in detail with reference to FIG. 12. When the registration range is expanded to the right and left directions, first, the rotation amount calculation unit 109 calculates the amount of positional shift, detects whether the registration range is expanded to the right or left, and transfers the determination result to the registration information selection unit 111. The registration information selection unit 111 determines whether there is generated an amount of positional shift which causes the registration range to be expanded, on the basis of the notified amount of positional shift. Where there is generated an amount of positional shift which causes the registration range to be expanded, the registration information selection unit 111 may update the registration candidate on the side to which direction the detection is performed, with new data, i.e., the new candidate.

Figure 12:
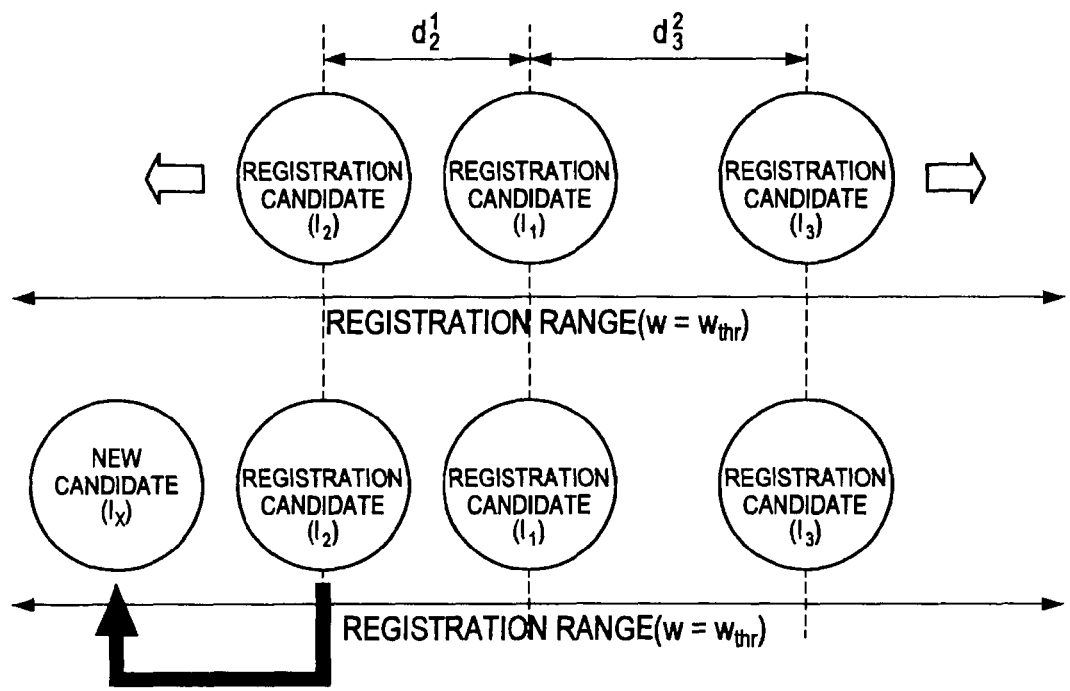
FIG. 12 is an explanatory diagram for illustrating a selection processing of registration information performed by the vein authentication apparatus according to the embodiment.

In other words, in the case shown in FIG. 12, the rotation amount calculation unit 109 determines that the rotational direction of the new candidate is left direction, and calculates the amount of rotation, i.e., the corresponding amount of positional shift, and notifies the amount of rotation to the registration information selection unit 111. After the registration information selection unit 111 determines that an amount of positional shift occurs through which the registration range is expanded, the registration information selection unit 111 updates the registration candidate $I_2$ with the new candidate $I_x$.

When the registration range is expanded to the right and left directions, there may be a case of an unfavorable registration example as shown in FIG. 3A and FIG. 3B. Such unfavorable case occurs when a finger is slightly rotated to one direction during registration and one registration candidate is made at that time, and thereafter, the finger is rotated only in the opposite direction so that the registration range is expanded. Also in this case, in the same manner as the case where the registration range is expanded to only one side, candidates at both ends of the registration range are kept as they are, and any one of the registration candidates existing therebetween is excluded from the candidates, so that the processing is performed for locating the registration candidates at an equal distance possible.

In other words, in the case shown in FIG. 12, while the registration information selection unit 111 holds the registration candidate $I_3$ and the new candidate $I_x$, the registration information selection unit 111 calculates $\Delta d$ for each of the registration candidate $I_1$ and the registration candidate $I_2$, and selects a registration candidate having a smaller $\Delta d$. As a result, as is evident from FIG. 12, the registration information selection unit 111 selects the registration candidate $I_1$, the registration candidate $I_3$, and the new candidate $I_x$ as registration information.

The method for selecting the registration information performed by the vein authentication apparatus 10 according to the present embodiment has been explained in detail hereinabove. Next, the method for registering the template according to the present embodiment will be described in detail with reference to FIG. 13 and FIG. 14.

[Explanation Using Flow Charts]

Figure 13:
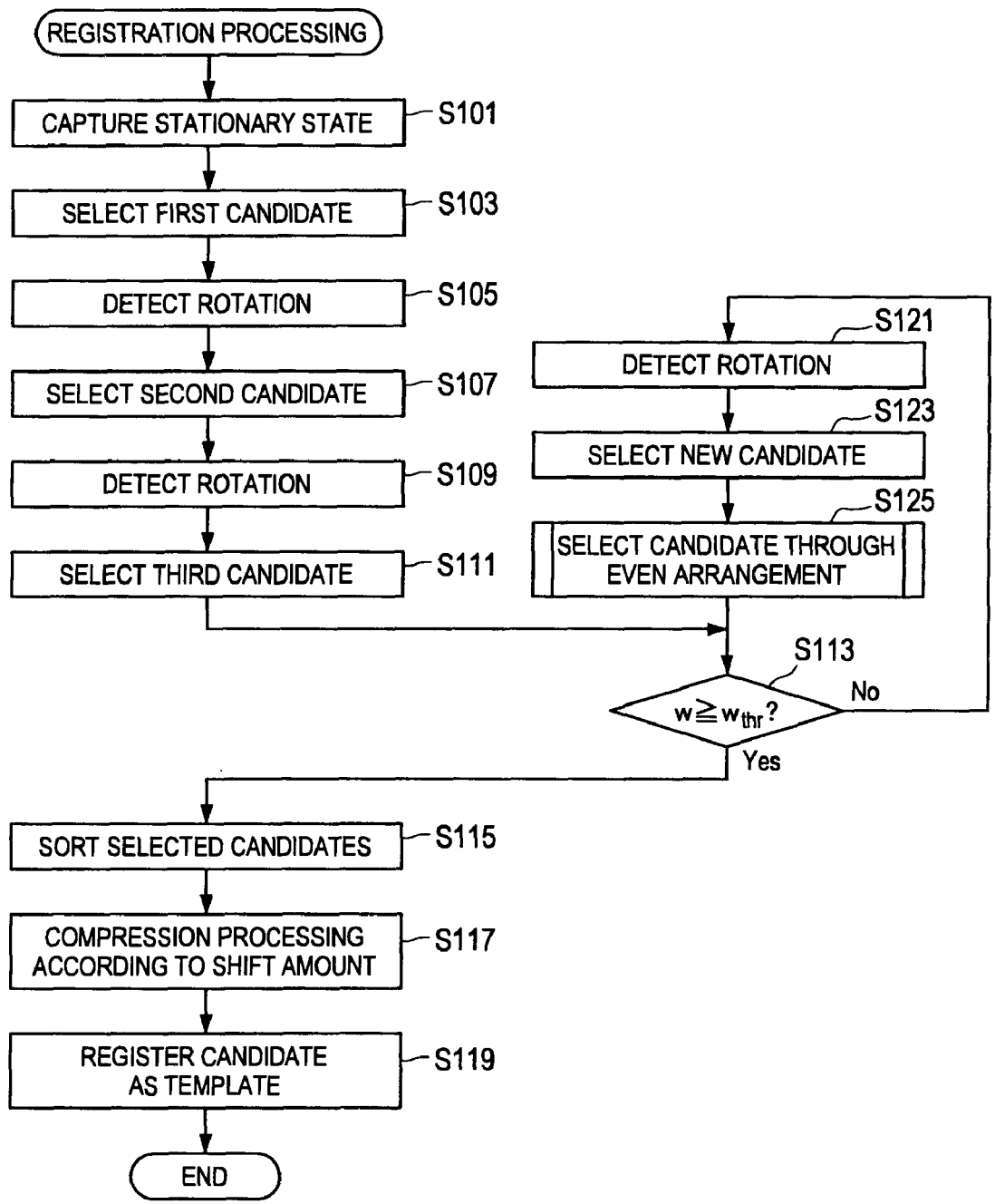
FIG. 13 is a flowchart for illustrating the template registration method according to the embodiment.
Figure 14:
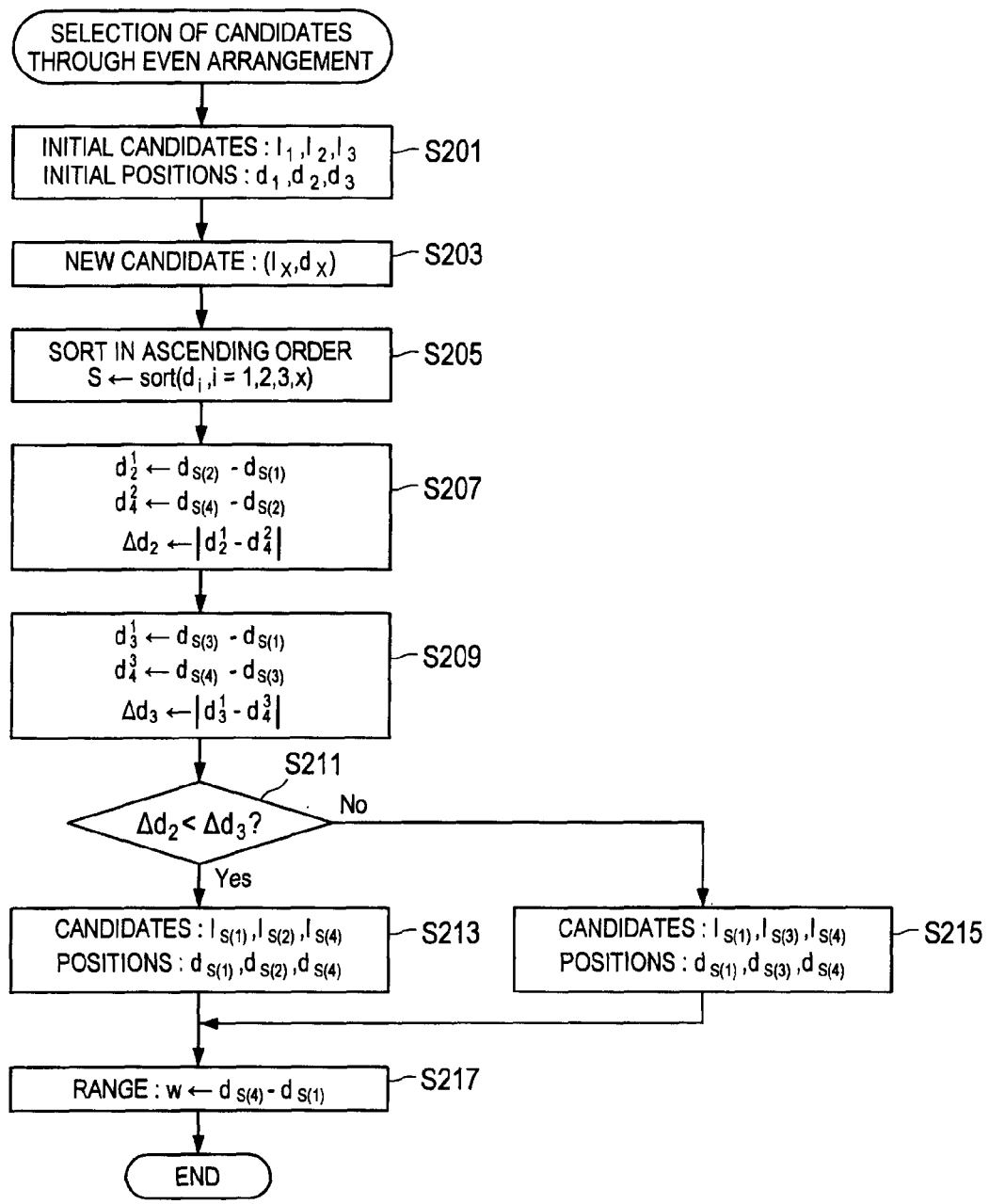
FIG. 14 is a flowchart for illustrating the selection processing of the registration information performed by the vein authentication apparatus according to the embodiment.

FIG. 13 is a flow chart for illustrating the template registration method according to the present embodiment. FIG. 14 is a flow chart for illustrating the selection processing of the registration information performed by the rotation amount calculation unit 109 and the registration information selection unit 111.

First, in the template registration method according to the present embodiment, the registration processing of the vein patterns starts when, e.g., a user inputs a command. When the registration processing starts, a display control unit (not shown) of the vein authentication apparatus 10 displays a message on a display unit to prompt the user to place and hold a finger on a predetermined position. When the registration processing starts, the light source unit 101 controlled by the imaging control unit 105 emits a near infrared light having a predetermined wavelength to the place on which the finger is placed. When the finger is determined to be placed and held still (step S101), the imaging unit 103 images the finger, and the imaging control unit 105 transfers the generated image data to the vein pattern extraction unit 107. Subsequently, the vein pattern extraction unit 107 extracts the vein pattern from the transferred image data. The extracted vein pattern is transferred to the rotation amount calculation unit 109 and the amount of positional shift and the like are calculated, which is transferred to the registration information selection unit 111. The registration information selection unit 111 selects the transferred first vein pattern as the first registration candidate (step S103).

Further, when the first registration candidate is selected, the display control unit (not shown) displays a graphic, an object, and the like showing, for example, a rotating finger on the display unit to prompt the user to begin to rotate his finger. The imaging unit 103 repeats imaging the finger surface at a predetermined time interval. Therefore, the user may freely move the finger without caring about the imaging interval of the vein authentication apparatus 10.

When the predetermined time passes and the imaging control unit 105 transfers the second image data, the vein pattern extraction unit 107 extracts a vein pattern from the second image data, and transfers the vein pattern to the rotation amount calculation unit 109. The rotation amount calculation unit 109 calculates a rotational direction and an amount of rotation for the second vein pattern transferred from the vein pattern extraction unit 107 (step S105), and records the rotational direction and the amount of rotation to the memory unit 119. Subsequently, the registration information selection unit 111 selects the second vein pattern as the registration information (step S107).

When the predetermined time passes and the imaging control unit 105 transfers the third image data, the vein pattern extraction unit 107 extracts a vein pattern from the third image data, and transfers the vein pattern to the rotation amount calculation unit 109. The rotation amount calculation unit 109 calculates a rotational direction and an amount of rotation for the third vein pattern transferred from the vein pattern extraction unit 107 (step S109), and records the rotational direction and the amount of rotation to the memory unit 119. Subsequently, the registration information selection unit 111 selects the third vein pattern as the registration information (step S111).

When the three pieces of registration information are selected, the registration information selection unit 111 determines whether a registration range w defined by the three pieces of registration information is equal to or more than the threshold value $w_{thr}$ of the registration range (step S113). When the registration range w is equal to or more than the threshold value $w_{thr}$, the registration information selection unit 111 notifies the determination result to the imaging control unit 105 to stop imaging, and selects the already selected three vein patterns as the registration information. The registration information selection unit 111 sorts the selected registration information on the basis of the absolute value of the amount of shift (step S115), and transfers the selected registration information to the registration information compression unit 113. The registration information compression unit 113 compresses the transferred registration information in accordance with the amount of shift (step S117), and transfers the compressed registration data to the template registration unit 115. The template registration unit 115 registers the notified registration information as the templates to the memory unit 119 (step S119), and terminates the registration processing.

When the registration range w is less than the threshold value $w_{thr}$, the imaging unit 103 images a finger surface, and the imaging control unit 105 transfers the fourth image data to the vein pattern extraction unit 107. Subsequently, the vein pattern extraction unit 107 extracts the vein pattern from the fourth image data, and transfers the vein pattern to the rotation amount calculation unit 109. The rotation amount calculation unit 109 calculates a rotational direction and an amount of rotation for the fourth vein pattern transferred from the vein pattern extraction unit 107 (step S121), and records the rotational direction and the amount of rotation to the memory unit 119. Subsequently, the registration information selection unit 111 selects the fourth vein pattern as the registration information.

Herein, the registration information selection unit 111 obtains from the memory unit 119 the information about the rotational direction and the amount of rotation of the three vein patterns already selected as the registration candidate, and selects the registration candidate on the basis of the information about the rotational direction and the amount of rotation for the new candidate (step S123). This selection processing will be explained in detail again with reference to FIG. 14. When the selected registration candidate is determined, the registration information selection unit 111 determines the registration range again (step S113).

Subsequently, the flow of the selection processing of the registration candidate by an even arrangement of the registration candidates will be explained in detail with reference to FIG. 14.

As described above, the registration information selection unit 111 obtains from the memory unit 119 the amount of rotation and the rotational direction for each of the first to third registration candidates (step S201). For example, the rotational direction and the amount of rotation can be represented as follows: a rotation from a reference position to the right direction is represented by a positive amount of rotation, and a rotation to the left direction is represented by a negative amount of rotation.

Subsequently, the registration information selection unit 111 also obtains a rotational direction and an amount of rotation for the new candidate (step S203).

Subsequently, the registration information selection unit 111 sorts the three registration candidates and the one new candidate in ascending order based on the amount of rotation (namely, the amount of positional shift) (step S205). For example, when the rotation to right direction is represented by a positive value as described above, with this sorting, candidates are sorted from a candidate at the right end to a candidate at the left end.

Subsequently, the registration information selection unit 111 calculates inter-candidate distances $d_2^1$ and $d_4^2$ for one candidate located on the inner side (for example, a candidate second from the right), and calculates $\Delta d_2$ (step S207). Similarly, the registration information selection unit 111 calculates inter-candidate distances $d_3^1$ and $d_4^3$ for another candidate located on the inner side (for example, a candidate second from the left), and calculates $\Delta d_3$ (step S209).

Subsequently, the registration information selection unit 111 compares the magnitudes of the calculated $\Delta d_2$ and $\Delta d_3$ (step S211). When $\Delta d_2$ is a smaller value, the registration information selection unit 111 does not hold the third candidate (for example, third from the right), and selects the first, second, and fourth candidates as the registration information (step S213). When $\Delta d_3$ is a smaller value, the registration information selection unit 111 does not hold the second candidate (for example, second from the right), and selects the first, third, and fourth candidates as the registration information (step S215).

Subsequently, the registration information selection unit 111 calculates the registration range w on the basis of the amount of rotation (amount of positional shift) of the registration information located at both ends (step S217).

As described above, the template registration method according to the present embodiment does not force a user to do any special movement for registering a template for biometric authentication, and further, it becomes possible to locate registration data at an equal distance within the range. As a result, more stable vein authentication processing can be performed. Further, by adopting the vein authentication method according to the present embodiment, it becomes possible to realize a registration system which can be used much more easily than an existing biometric authentication system.

<Update of Registered Information During Authentication Processing>

In the above-described template registration method, the registration of the templates is finished at the moment when the registration range w is covered (i.e., at the moment when $w \geq w_{thr}$) as is evident from step S113 of FIG. 13. This is because there is a possibility that the registration processing places a burden on a user when, at the time of registration, the registration processing is set so that the registration processing is not to be finished until all of the registration candidates are located at an equal distance. Therefore, there is a possibility that at the moment when the three vein patterns are selected, which are extracted first, the registration processing is finished without performing the registration selection by an even arrangement of the registration candidates, and there may be a case where the registration candidates are not located at an equal distance in an absolute manner.

In view of the above circumstances, by updating the registered template by use of the vein pattern used during the authentication processing, it becomes possible to correct a blind section that may be generated at the time of the registration during the authentication. The update processing of the registration information during this authentication processing will be hereinafter explained in detail.

A case will be considered where, during the registration of the templates, the processing is not performed so that the registration information is strictly located at an equal distance and where the authentication is successful upon detecting a positional shift from the information (template) registered at the time of the authentication of the vein pattern. The vein pattern authentication unit 117 calculates the correlation coefficient during the authentication of the vein pattern, and therefore, can calculate the amount of positional shift (i.e, the rotational direction and the amount of rotation) of the vein pattern which is input for the authentication. Therefore, when the authentication is successful, the vein pattern authentication unit 117 transfers the successfully authenticated vein pattern (hereinafter referred to as authentication information) to the registration information selection unit 111.

When the registration information selection unit 111 receives the authentication information, the registration information selection unit 111 uses the amount of positional shift in the authentication information and the currently registered registration information and calculates a relative positional relationship of the above information. When the authentication information contributes to an even arrangement of the registration candidates better than the currently registered registration information, the registration information selection unit 111 performs the selection processing on the above registration information and updates the template by replacing the already registered registration information with the information (authentication information) presented for the authentication. However, the registration information according to the present embodiment has a different compression rate according to the absolute value of the amount of shift, and therefore, the template is updated only when the registration information to be replaced has the same amount of data as the replaced registration information.

At this moment, it is to be taken into consideration that the update of the template, which causes the registration range to be expanded, is not to be performed. Such update may make the blind section larger.

Figure 15:
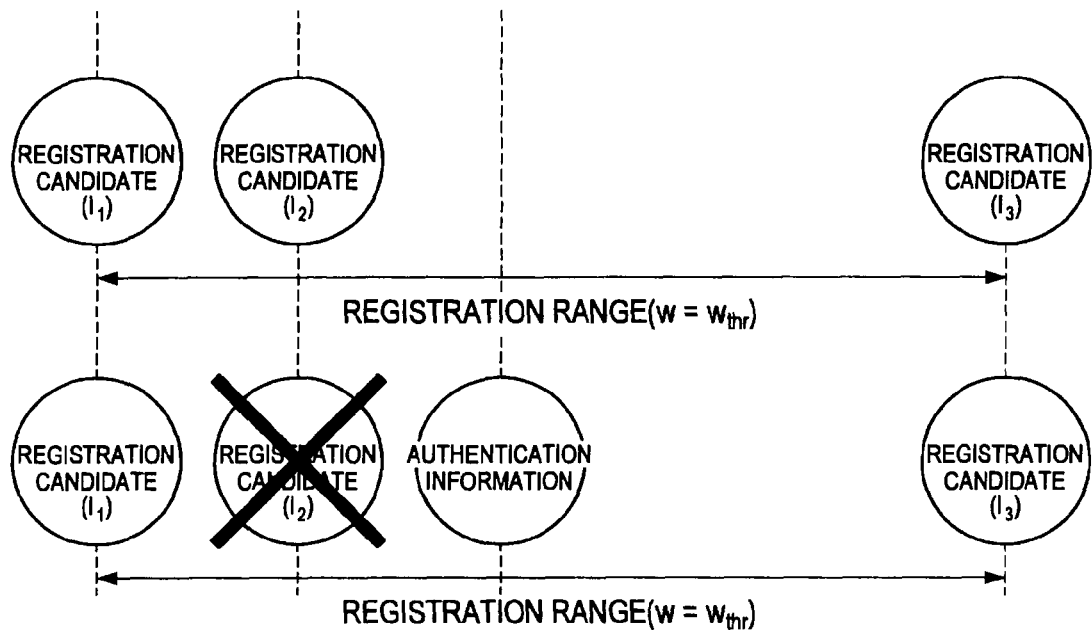
FIG. 15 is an explanatory diagram for illustrating an update of the registration information during an authentication processing.

FIG. 15 is an explanatory diagram for illustrating the update of the registration information during the authentication processing. As shown by the example in the upper row of FIG. 15, a case will be considered where the registration information $I_1$ to the registration information $I_3$ are already registered as templates, and there is a blind section between the registration information $I_2$ and the registration information $I_3$. In this case, when the vein authentication processing is performed and results in successful authentication, the vein pattern authentication unit 117 notifies the successfully authenticated vein pattern to the registration information selection unit 111.

First, the registration information selection unit 111 determines whether the notified authentication information is located between the registration information $I_1$ and the registration information $I_3$ shown in the upper row of FIG. 15. When the notified authentication is determined to be located outside of the registration information $I_1$ and the registration information $I_3$, there may occur an update causing the registration range to be expanded as described above, and in addition a blind section may become larger.

For example, when the authentication information notified to the registration information selection unit 111 is located in the position indicated in the lower row of FIG. 15, this situation does not correspond to the update which causes the registration range to be expanded. Therefore, the registration information selection unit 111 performs the update processing of the registration information by using the already registered registration information $I_1$ to the already registered registration information $I_3$ and the notified authentication information. This update processing of the registration information is performed according to the same procedure as the selection processing of the registration information during the registration of the templates.

For example, as shown in the lower row of FIG. 15, when the authentication information contributes to an even arrangement of the registration candidates better than the registration information $I_2$ as a result of the update processing, the registration information selection unit 111 selects the authentication information as the registration information instead of the registration information $I_2$.

[Explanation Using Flowchart]

Figure 16:
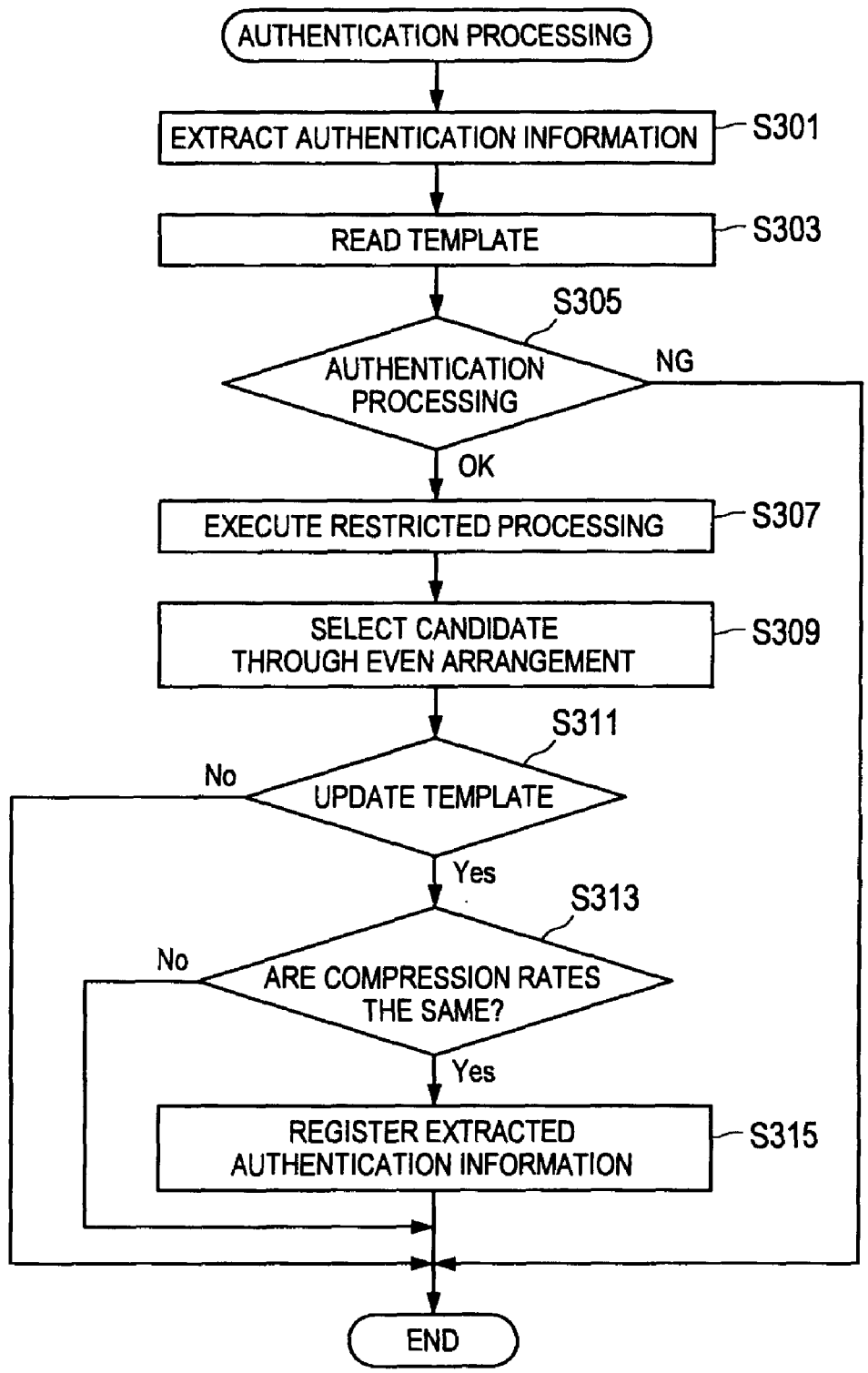
FIG. 16 is a flowchart for illustrating an updating method of the registration information during the authentication processing.

FIG. 16 is a flowchart for illustrating the update of the registration information during the authentication processing.

First, the authentication processing itself of the vein pattern starts when, e.g., a user inputs a command. When the authentication processing starts, the display control unit (not shown) of the vein authentication apparatus 10 displays a message on the display unit to prompt the user to place a finger on a predetermined position. When the authentication processing starts, the light source unit 101 controlled by the imaging control unit 105 emits a near infrared light having the predetermined wavelength to the place on which the finger is placed. Then, the imaging unit 103 images the finger, and the imaging control unit 105 transfers the generated image data to the vein pattern extraction unit 107. Subsequently, the vein pattern extraction unit 107 extracts the vein pattern from among the transferred image data (step S301). The extracted vein pattern is notified to the vein pattern authentication unit 117.

First, the vein pattern authentication unit 117 reads the templates recorded in the memory unit 119 (step S303), and compares the extracted vein pattern with the registered templates. More specifically, the vein pattern authentication unit 117 calculates the correlation coefficient shown in Formula 4, and determines whether the obtained correlation coefficient is more than a predetermined threshold value (step S305). When the correlation coefficient is less than the predetermined threshold value, the vein pattern authentication unit 117 determines that the extracted vein pattern is not to similar to the registered template, and determines that the authentication has failed.

When the obtained correlation coefficient is equal to or more than the predetermined threshold value, the vein pattern authentication unit 117 determines that the extracted vein pattern is similar to the registered template, and determines that the authentication is successful.

When the authentication is successful, the vein pattern authentication unit 117 notifies the successful authentication to a processing unit controlling a processing whose execution is restricted, so that the processing unit carries out the processing whose execution was restricted (step S307).

When the authentication is successful, the vein pattern authentication unit 117 notifies the successfully authenticated vein pattern (the authentication information) to the registration information selection unit 111. The registration information selection unit 111 selects a candidate by an even arrangement of the registration candidates (step S309). More specifically, a determination is first made as to whether the notified authentication information is not located in a position which causes the registration range to be expanded, and determines whether the registration information is to be updated or not in accordance with the flowchart shown in FIG. 14 (step S311).

When the authentication information is selected instead of the already registered registration information as a result of the determination, the registration information selection unit 111 compares the compression rates (or the amount of data) between the selected authentication information and the registration information to be updated (step S313). When the compression rates (i.e., the amount of data) are the same, the selection result is notified to the template registration unit 115. The template registration unit 115 newly registers the authentication information as the registration information (step S315). When the authentication information is not selected as the new registration information, or when the compression rates differ from each other, the processings are terminated without updating the template.

As described above, by performing the update processing of the registration information during the authentication, the template is updated so as to reduce the blind section. Every time the authentication is performed, templates get "mature".

In the above explanation according to each embodiment of the present invention, three vein patterns are registered as the registration information. However, the same processings can be performed even when four or more vein patterns are selected as the registration information. In other words, while the vein patterns located at both ends of the registration range are kept, distances to the remaining vein patterns may be calculated for each of the vein patterns located in the inside, and a vein pattern having almost same distances to the adjacent vein patterns may be selected as the registration candidate.

<Hardware Configuration>

Figure 17:
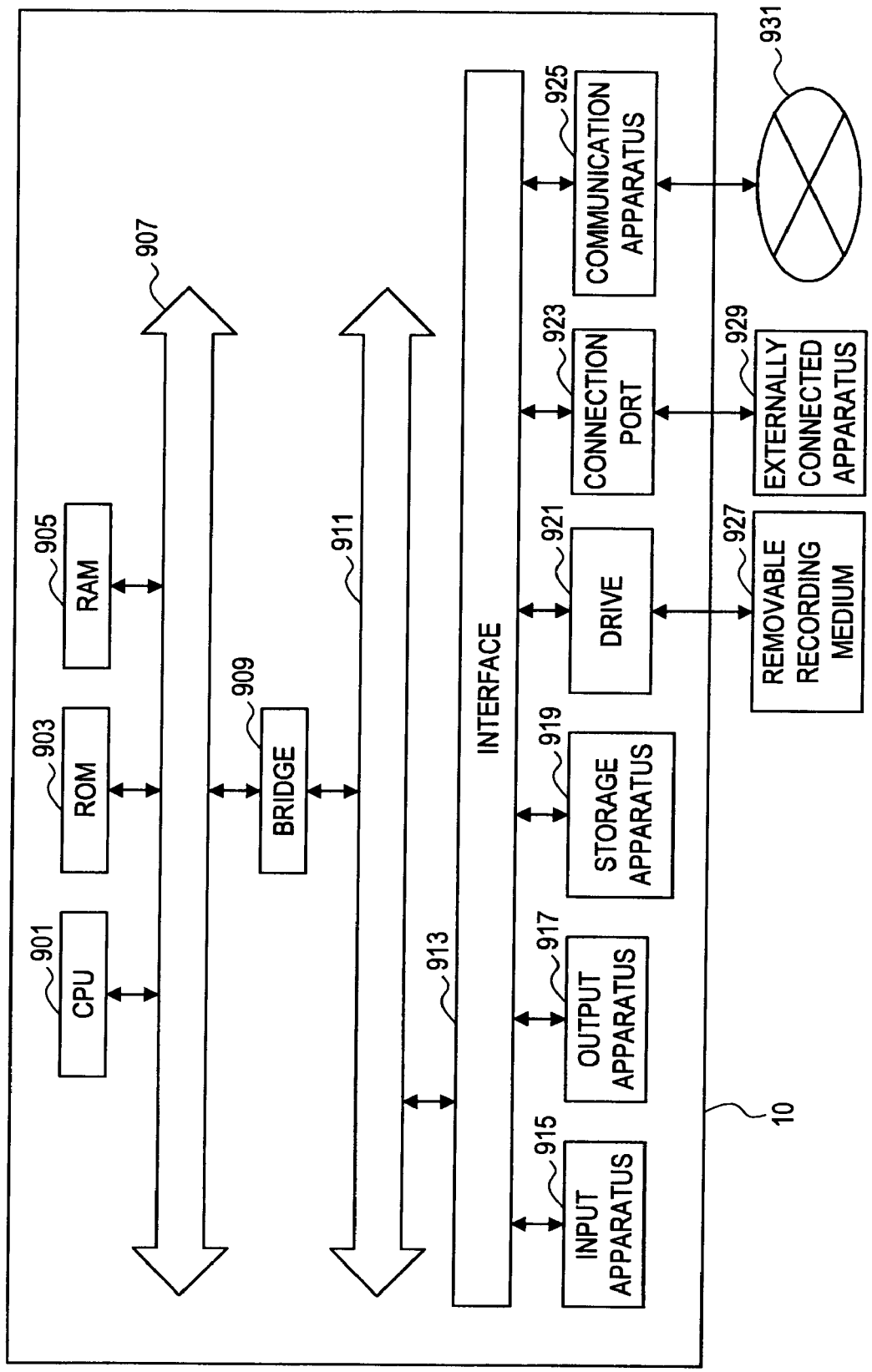
FIG. 17 is a block diagram for illustrating a hardware configuration of the vein authentication apparatus according to the embodiment.

Next, the hardware configuration of the vein authentication apparatus 10 according to each embodiment of the present invention will be described in detail with reference to FIG. 17. FIG. 17 is a block diagram for illustrating the hardware configuration of the vein authentication apparatus 10 according to each embodiment of the present invention.

The vein authentication apparatus 10 mainly includes a CPU 901, a ROM 903, and a RAM 905. Further, the vein authentication apparatus 10 includes a host bus 907, a bridge 909, an external bus 911, an interface 913, an input apparatus 915, an output apparatus 917, a storage apparatus 919, a drive 921, a connection port 923, and a communication apparatus 925.

The CPU 901 serves as an arithmetic processing apparatus and control apparatus and controls overall operation or a portion of operation in the vein authentication apparatus 10 in accordance with various programs recorded in the ROM 903, the RAM 905, the storage apparatus 919, or a removable recording medium 927. The ROM 903 stores programs, operation parameters, and the like used by the CPU 901. The RAM 905 primarily stores programs used in execution of the CPU 901 and parameters and the like varying during the execution as necessary. These are connected with each other via the host bus 907 constituted by an internal bus such as a CPU bus and the like.

The host bus 907 is connected to the external bus 911 such as a PCI (Peripheral Component Interconnect/Interface) via the bridge 909.

The input apparatus 915 is operation means operated by a user, such as a mouse, a keyboard, a touch panel, buttons, switches and levers. The input apparatus 915 may be remote control means (a so-called remote controller) using, for example, infrared light and other radio waves, or may be an externally connected apparatus 929 such as a portable telephone and a PDA for operating the vein authentication apparatus 10. The input apparatus 915 generates an input signal on the basis of, for example, information which is input by a user with the above operation means, and is constituted by an input control circuit for outputting input signals to the CPU 901. A user of the vein authentication apparatus 10 can input various data to the vein authentication apparatus 10 and can instruct the vein authentication apparatus 10 to perform processings and operation by operating this input apparatus 915.

The output apparatus 917 is constituted by an apparatus capable of audibly or visually notifying obtained information to a user. Examples of the output apparatus 917 include display apparatuses such as a CRT display apparatus, a liquid crystal display apparatus, a plasma display apparatus, an EL display apparatus, and lamps, audio output apparatuses such as a speaker and a headphone, a printer, a portable telephone, and a facsimile machine. The output apparatus 917 outputs a result obtained from various processings performed by, for example, the vein authentication apparatus 10. More specifically, the display apparatus displays a result as texts or images, which is obtained from various processings performed by the vein authentication apparatus 10. On the other hand, the audio output apparatus converts an audio signal such as reproduced audio data and sound data into an analog signal, and outputs the analog signal.

The storage apparatus 919 is an example of a memory unit of the vein authentication apparatus 10 and is used to store data. The storage apparatus 919 is constituted by, for example, a magnetic storage device such as a HDD (Hard Disk Drive), a semiconductor storage device, an optical storage device, or a magneto-optical storage device. This storage device 919 stores, e.g., programs and various data executed by the CPU 901 and various data obtained from the outside.

The drive 921 is a reader/writer for recording medium, and is embedded in the vein authentication apparatus 10 or attached externally thereto. The drive 921 reads information recorded in the attached removable recording medium 927 such as a magnetic disk, an optical disk, a magneto-optical disk, or a semiconductor memory, and outputs the read information to the RAM 905. The drive 921 can write in the attached removable recording medium 927 such as a magnetic disk, an optical disk, a magneto-optical disk, or a semiconductor memory, and outputs the read information to the RAM 905. The removable recording medium 927 is, for example, a DVD medium, an HD-DVD medium, and a Blu-ray medium. The removable recording medium 927 may be a CompactFlash (registered trademark) (CompactFlash: CF), a memory stick, an SD memory card (Secure Digital Memory Card), or the like. Alternatively, the removable recording medium 927 may be, for example, an IC card (Integrated Circuit Card) equipped with a non-contact IC ship or an electronic appliance.

The connection port 923 is a port for allowing apparatuses to directly connect to the vein authentication apparatus 10. Examples of the connection port 923 include a USB (Universal Serial Bus) port, an IEEE1394 port such as i.Link, a SCSI (Small Computer System Interface) port, and the like. Other examples of the connection port 923 include an RS-232C port, an optical audio terminal, an HDMI (High-Definition Multimedia Interface) port, and the like. When the externally connected apparatus 929 is connected to this connection port 923, the vein authentication apparatus 10 directly obtains various data from the externally connected apparatus 929 and provides various data to the externally connected apparatus 929.

The communication apparatus 925 is a communication interface constituted by, for example, a communication device for connecting to a communication network 931. The communication apparatus 925 is, for example, a wired or wireless LAN (Local Area Network), Bluetooth, a communication card for WUSB (Wireless USB), or the like. Alternatively, the communication apparatus 925 may be a router for optical communication, a router for ADSL (Asymmetric Digital Subscriber Line), a model for various communications, or the like. This communication apparatus 925 can transmit and receive signals and the like in accordance with a predetermined protocol such as TCP/IP, for example, on the Internet and with other communication apparatuses. The communication network 931 connected to the communication apparatus 925 is constituted by a network and the like, which is connected via wire or wirelessly. For example, the communication network 931 may be the Internet, a home LAN, an infrared communication, a radio wave communication, a satellite communication, or the like.

An example of hardware configuration capable of achieving the functions of the vein authentication apparatus 10 according to each embodiment of the present invention has been described hereinabove. Each of the above constituent elements may be made using a generally-used member, or may be made with hardware dedicated for the function of the constituent element. Therefore, the used hardware configuration can be changed as necessary in accordance with the state of art at the time of carrying out the present embodiment.

SUMMARY

As described above, the vein authentication apparatus and the template registration method according to this method does not force a user to do any special movement for registering a template for biometric authentication, and further, allows to locate registration data at an equal distance within the range so as to achieve a stable authentication processing.

Further, the order of templates is changed so that a template in which an amount of shift has the smallest absolute value is to be the first collated template among the plurality of templates, and when compressing the first collated information, the compression rate is lowered compared with that of other information. Thereby, much information can be hold, and the vein pattern can be converted into a template with less information being lost in the compression processing, so that the authentication succeeds more easily with the first template. As a result, the same level of stability as a method in related art is maintained, and further, although a plurality of templates are hold, the authentication processing is actually more likely to be completed with the first template. Therefore, the authentication speed can be improved, and an easy-to-use interface can be realized.

It should be understood by those skilled in the art that various modifications, combinations, sub-combinations and alterations may occur depending on design requirements and other factors insofar as they are within the scope of the appended claims or the equivalents thereof.

The present application contains subject matter related to that disclosed in Japanese Priority Patent Application JP 2009-024239 filed in the Japan Patent Office on Feb. 4, 2009, the entire content of which is hereby incorporated by reference.

What is claimed is:

1. A vein authentication apparatus comprising:
   a light source unit for emitting a near infrared light having a predetermined wavelength to a surface of a finger rotating on its axis in a longitudinal direction;
   an imaging unit for imaging the finger surface, to which the near infrared light is emitted, at a predetermined time interval, and for generating a plurality of vein image data whose imaging ranges are different from each other;
   a vein pattern extraction unit for extracting a vein pattern from each of the plurality of vein image data;
   a rotational amount calculation unit for calculating a rotational direction and an amount of rotation of the finger associated with the rotational movement for each of the extracted vein patterns by using an imaging range of one of the vein patterns as a reference;
   a registration information selection unit for:
      calculating a shift width of the imaging range on the basis of the rotational direction and the amount of rotation,
      determining whether the shift width of the imaging range is equal to or more than a predetermined threshold value,
      selecting a vein pattern to be registered as a template from among the plurality of vein patterns when the shift width of the imaging range is less than the predetermined threshold value, and
      setting the selected vein pattern as registration information; and
   a registration information compression unit for compressing, in accordance with the shift width of the imaging range, selected registration information when the shift width of the imaging range is equal to or more than the predetermined threshold value.

2. The vein authentication apparatus according to claim 1, wherein the registration information selection unit sorts the plurality of pieces of registration information selected when the shift width of the imaging range is equal to or more than the predetermined threshold value, in ascending order from the registration information in which the amount of rotation has the smallest absolute value.

3. The vein authentication apparatus according to claim 2, wherein the registration information compression unit causes an amount of data allocated for registering the registration information in which the amount of rotation has the smallest absolute value among the plurality of pieces of registration information, to be larger than an amount of data allocated for registering the other of the plurality of pieces of registration information.

4. The vein authentication apparatus according to claim 2, wherein the registration information compression unit causes a compression rate of the registration information in which the amount of rotation has the smallest absolute value among the plurality of pieces of registration information, to be lower than a compression rate of the other of the plurality of pieces of registration information.

5. The vein authentication apparatus according to claim 1, wherein the registration information selection unit holds the vein patterns located at both ends of the imaging range, and selects a vein pattern located in a position from which distances to adjacent registration candidates are close to be equal from among the vein patterns existing between the vein patterns located at the both ends.

6. The vein authentication apparatus according to claim 5, further comprising a vein pattern authentication unit for authenticating the extracted vein pattern on the basis of the registration information registered as the template,
wherein the registration information selection unit updates the content of the already registered registration information by using the registration information and the authenticated vein pattern.

7. The vein authentication apparatus according to claim 1, wherein the rotational amount calculation unit calculates a correlation coefficient between the one of the vein patterns serving as the reference and the other of the vein patterns, and calculates the rotational direction and the amount of rotation on the basis of a shift direction and an amount of shift at a peak position of the correlation coefficient.

8. The vein authentication apparatus according to claim 1, wherein the threshold value of the shift width in the imaging range is 10% of pixels representing an imaging range of the one of the vein patterns serving as the reference.

9. A template registration method, comprising:
emitting a near infrared light having a predetermined wavelength to a surface of a finger rotating on its axis in a longitudinal direction;
imaging the finger surface, to which the near infrared light is emitted, at a predetermined time interval, and generating a plurality of vein image data whose imaging ranges are different from each other;
extracting a vein pattern from each of the plurality of vein image data;
calculating a rotational direction and an amount of rotation of the finger associated with the rotational movement for each of the extracted vein patterns by using an imaging range of one of the vein patterns as a reference;
calculating a shift width of the imaging range on the basis of the rotational direction and the amount of rotation, determining whether the shift width of the imaging range is equal to or more than a predetermined threshold value, selecting the vein pattern to be registered as a template from among the plurality of vein patterns when the shift width of the imaging range is less than the predetermined threshold value, and setting the selected vein pattern as registration information; and
compressing, in accordance with the shift width of the imaging range, the selected registration information when the shift width of the imaging range is equal to or more than the predetermined threshold value.

* * * * *